US007109360B1

(12) United States Patent
Kuenzer et al.

(10) Patent No.: US 7,109,360 B1
(45) Date of Patent: Sep. 19, 2006

(54) 16-HYDROXYESTRATRIENES AS SELECTIVELY ACTIVE ESTROGENS

(75) Inventors: Hermann Kuenzer, Berlin (DE); Rudolf Knauthe, Berlin (DE); Monika Lessl, Berlin (DE); Karl-Heinrich Fritzemeier, Berlin (DE); Christa Hegele-Hartung, Muelheim a.d. Ruhr (DE); Ulf Boemer, Berlin (DE); Gerd Mueller, Jena (DE); Dirk Kosemund, Erfurt (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 09/497,891

(22) Filed: Feb. 4, 2000

Related U.S. Application Data

(60) Provisional application No. 60/131,268, filed on Apr. 27, 1999.

(30) Foreign Application Priority Data

Feb. 9, 1999 (DE) ................. 199 06 159

(51) Int. Cl.
*C07J 9/00* (2006.01)
*C07J 41/00* (2006.01)

(52) U.S. Cl. ................. 552/553; 552/554; 552/515; 552/618; 552/625; 552/626; 552/630; 514/169; 514/179; 514/182

(58) Field of Classification Search .............. 552/621, 552/545, 553, 554, 626, 625, 630, 179, 169, 552/182; 514/182, 177, 179, 169
See application file for complete search history.

(56) References Cited

U.S. PATENT DOCUMENTS

| 2,779,773 A | 1/1957 | Huffman |
| 3,282,786 A | 11/1966 | Muller |

FOREIGN PATENT DOCUMENTS

| CH | 537916 | 7/1973 |
| CH | 538460 | 8/1973 |
| FR | 5099 M | 5/1967 |
| GB | 823955 | 11/1959 |
| WO | 9708188 | * 3/1997 |

OTHER PUBLICATIONS

Siebert et al. (DN 110:75884, HCAPLUS, abstract of DD 253249).*
Anner, George et al. (DN79:137383, HCAPLUS, abstract of CH 537916).*
DN:126:225448, HCAPLUS, abstract of WO9708188.*
Miki et al. (DN 89:197804, CAPLUS, abstract of JP 53065865).*
Anner et al. (DN 79:137384, CAPLUS, abstract of CH 538460).*
Fishman et al., Document #: 53:17432, CAPLUS, Abstract of Journal of Organic Chemistry (1958), 23, 1190-2.*
Fishman et al., Document #: 52:93818, CAPLUS, Abstract of Journal of Biological Chemistry (1958), 232, 729-36.*
Arunachalam et al., "Iodoestrogens, syntheses, and interaction with uterine receptors." Journal of Biological Chemistry, col. 254(13), pp. 5900-5905, 1979.*
AN 1970:3637 CAPLUS, DN: 72:3637 (ROUSSEL-UCLAF).*
AN 1979:66957 CAPLUS, DN: 90:66957 (OJASOO et al).*
AN 1998:559789 CAPLUS, DN: 129:306174 (BARBER et al).*
G. Stack et al: "Relative Mitogenic Activities of Various Estrogens and Antiestrogens" STEROIDS., Bd. 54, Nr.2, Aug. 1989, pp. 227-243.
T.E. Wiese et al: "Introduction of the Estrogen Specific Mitogenic Response of MCF-& Cells by selected Analogues of Estradui-17. beta: A 3D QSAR Study" Journal of Medical Chemistry, Bd. 40, Nr. 22, Oct. 24, 1997 pp. 3659-3669.
Anstead G M et al: The Estradiol pharmacophore: Ligand structure-estrogen receptor binding affinity relationships and a model for the receptor binding site Steroids: Stucture, Function, and Regulation, US, Elsevier Science Publishers, Bd. 62, Nr. 3, Mar. 1, 1997 pp. 268-303.
Tedesco R et al.: "7 alpha, 11 beta-disubstituted estrogens: probes for the shape of the ligand binding pocket in the estrogen receptor" Bioorganic & Medicinal Chemistry Letters, Bd. 7 , Nr. 22, Nov. 1997, pp. 2919-2924.
R.B. Gabbard et al: "Structure Activity Relationships of Estrogens. Effects of 14-Dehysrogenation and Axial Methyl Groups at C-7, C-9 and C-11" STEROIDS., Bd. 41, Nr. 6, Jun. 1983, pp. 791-794.

* cited by examiner

*Primary Examiner*—Sabiha N. Qazi
(74) *Attorney, Agent, or Firm*—Millen, White, Zelano & Branigan, P.C.

(57) ABSTRACT

The invention describes new compounds as pharmaceutical active ingredients, which have in vitro a higher affinity to estrogen receptor preparations from rat prostates than to estrogen receptor preparations from rat uteri and in vivo a preferential action on bone rather than the uterus, their production, their therapeutic use and pharmaceutical dispensing forms that contain the new compounds.

The new compounds are 16α- and 16β-hydroxy-estra-1,3,5(10)-estratrienes, which carry additional substituents on the steroid skeleton and can have one or more additional double bonds in the B-, C- and/or D-rings.

13 Claims, No Drawings

16-HYDROXYESTRATRIENES AS SELECTIVELY ACTIVE ESTROGENS

This application claims the benefit of the filing date of U.S. Provisional Application Ser. No. 60/131,268 filed Apr. 27, 1999.

FIELD OF THE INVENTION

This invention relates to new compounds as pharmaceutical active ingredients, which have in vitro a higher affinity to estrogen receptor preparations from rat prostates than to estrogen receptor preparations from rat uteri and in vivo a preferential action on bone rather than the uterus, their production, their therapeutic use and pharmaceutical dispensing forms that contain the new compounds.

The chemical compounds are novel, steroidal, tissue-selective estrogens.

BACKGROUND OF THE INVENTION

Established estrogen therapies for treatment of hormone-deficiency-induced symptoms and the protective action of estrogens on bones, brains, vessels and other organ systems.

The efficiency of estrogens in the treatment of hormone-deficiency-induced symptoms such as hot flashes, atrophy of estrogen target organs and incontinence, as well as the successful use of estrogen therapies for prevention of bone mass loss in peri- and postmenopausal women, is well documented and generally accepted (Grady et al. 1992, Ann Intern Med 117: 1016–1037). It is also well documented that estrogen replacement therapy in postmenopausal women or in women with ovarian dysfunction that is caused in some other way reduces the risk of cardiovascular diseases compared to non-estrogen-treated women (Grady et al., loc. cit.).

In addition, more recent studies confirm a protective action of estrogens against neurodegenerative diseases, such as, e.g., Alzheimer's disease (Henderson 1997, Neurology 48 (Suppl 7): S27–S35; Birge 1997, Neurology 48 (Suppl 7): S36–S41), a protective action with respect to brain functions, such as memory and learning capacity (McEwen et al. 1997, Neurology 48 (Suppl 7): S8–S15; Sherwin 1997, Neurology 48 (Suppl 7): S21–S26), as well as against hormone-deficiency-induced mood swings (Halbreich 1997, Neurology 48 (Suppl 7): S16–S20).

In addition, estrogen replacement therapy has proven effective relative to the reduction of the incidence of colorectal carcinoma (Calle, E. F. et al., 1995, J Natl Cancer Inst 87: 517–523).

In conventional estrogen or hormone replacement therapy (=HRT), natural estrogens, such as estradiol, and conjugated estrogens that consist of equine urine are used either by themselves or in combination with a gestagen. Instead of the natural estrogens, derivatives that are obtained by esterification, such as, e.g., 17β-estradiol-valerate, can also be used.

Because of the stimulating action of the estrogens that are used on the endometrium, which results in an increase of the risk of endometrial carcinoma (Harlap, S. 1992, Am J Obstet Gynecol 166: 1986–1992), estrogen/gestagen combination preparations are preferably used in hormone replacement therapy. The gestagenic component in the estrogen/gestagen combination avoids hypertrophy of the endometrium, but the occurrence of undesirable intracyclic menstrual bleeding is also linked to the gestagen-containing combination.

Selective estrogens represent a more recent alternative to the estrogen/gestagen combination preparations. Up until now, selective estrogens have been defined as those compounds that have an estrogen-like effect on the brain, bones and vascular system, owing to their antiuterotrophic (i.e., antiestrogenic) partial action, but they do not have a proliferative effect on the endometrium.

A class of substances that partially meet the desired profile of a selective estrogen are the so-called "Selective Estrogen Receptor Modulators" (SERM) (R. F. Kauffman, H. U. Bryant 1995, DNAP 8 (9): 531–539). In this case, there are partial agonists of estrogen receptor subtype "ERα." This substance type is ineffective, however, with respect to the therapy of acute postmenopausal symptoms, such as, e.g., hot flashes. As an example of a SERM, the raloxifene that was recently introduced for the indication of osteoporosis can be mentioned.

Estrogen Receptor Beta (ERβ)

Estrogen receptor β (ERβ) was recently discovered as a second subtype of the estrogen receptor (Kuiper et al. (1996), Proc. Natl. Acad. Sci. 93: 5925–5930; Mosselman, Dijkema (1996) Febs Letters 392: 49–53; Tremblay et al. (1997), Molecular Endocrinology 11: 353–365). The expression pattern of ERβ differs from that of the ERα (Kuiper et al. (1996), Endocrinology 138: 863–870). ERβ thus predominates over ERα in the rat prostate, while ERα predominates over ERβ in the rat uterus. Areas in which in each case only one of the two ER-subtypes is expressed were identified in the brain (Shugrue et al. (1996), Steroids 61: 678–681; Li et al. (1997), Neuroendocrinology 66:63–67). ERβ is expressed in, i.a., areas that are considered to be important for cognitive processes and "mood" (Shugrue et al. 1997, J Comparative Neurology 388: 507–525).

Other organ systems with comparatively higher ERβ-expression comprise the bones (Onoe, Y. et al., 1997, Endocrinology 138: 4509–4512), the vascular system (Register, T. C., Adams, M. R. 1998, J. Steroid Molec Biol 64: 187–191), the urogenital tract (Kuiper, G. J. M. et al. 1997, Endocrinology 138: 863–870), the gastrointestinal tract (Campbell-Thopson 1997, BBRC 240: 478–483), as well as the testis (Mosselmann, S. et al. 1996 Febs Lett 392 49–53) including the spermatides (Shugrue et al. 1998, Steroids 63: 498–504). The tissue distribution suggests that estrogens regulate organ functions via ERβ. The fact that ERβ is functional in this respect also follows by studies in ERα-(ERKO) or ERβ-(βERKO)-knockout mice: ovariectomy produces bone mass loss in ERKO-mice, which can be cancelled out by estrogen substitution (Kimbro et al. 1998, Abstract OR7-4, Endocrine Society Meeting New Orleans). Estradiol in the blood vessels of female ERKO mice also inhibits vascular media and smooth muscle cell proliferation (Iafrati, M. D. et al. 1997, Nature Medicine 3: 545–548). These protective actions of estradiol are carried out in the ERKO mouse presumably via ERβ.

Observations of βERKO mice provide an indication on a function of ERβ in the prostate and bladder: in the case of older male mice, symptoms of prostate and bladder hyperplasia occur (Krege, J. H. et al. 1998, Proc Natl Acad Sci 95: 15677–15682). In addition, female ERKO mice (Lubahn, D. B. et al. 1993, Proc Natl Acad Sci 90: 11162–11166) and male ERKO mice (Hess, R. A. et al. 1997, Nature 390: 509–512) as well as female βERKO mice (Krege, J. H., 1998) have fertility disorders. Consequently, the important function of estrogens with respect to maintaining testis and ovary functions as well as fertility is confirmed.

Westerlind et al., 1998, describe a differential action of 16α-hydroxyestrone on the bones, on the one hand, and reproductive organs of female rats, on the other (Westerlind et al. 1998, J Bone and Mineral Res 13: 1023–1031).

Some studies showed that 16α-hydroxyestrone binds three times better to the human estrogen receptor β (ERβ) than to the human estrogen receptor α (ERα). The RBA value of the substance on the rat prostate estrogen receptor is five times better than the RBA value of the substance on the rat uterus estrogen receptor. According to some findings, the dissociation of the substance that is described by Westerlind can be attributed to their preference for ERβ rather than ERα.

It was possible to achieve a selective estrogen action on specific target organs by subtype-specific ligands based on the different tissue or organ distribution of the two subtypes of the ERs. Substances with a preference for ERβ compared to ERα in the in vitro receptor binding test were described by Kuiper et al. (Kuiper et al. (1996), Endocrinology 138: 863–870). A selective action of subtype-specific ligands of the estrogen receptor on estrogen-sensitive parameters in vivo was not previously shown.

The object of this invention is therefore to prepare compounds that have in vitro a dissociation with respect to the binding to estrogen receptor preparations from rat prostates and rat uteri and that have in vivo a dissociation with respect to bones rather than the uterus action. The compounds are to have in vitro a higher affinity to estrogen receptor preparations from rat prostates than to estrogen receptor preparations from rat uteri and in vivo a many times higher potency with respect to protection against hormone-deficiency-induced bone mass loss in comparison to uterus-stimulating action.

In the broader sense, a structure-action relationship, which allows for access to compounds that have the above-formulated pharmacological profile of better estrogenic action on bones than on the uterus, is to be made available by this invention.

According to the invention, the object above is achieved by the provision of 16α- and 16β-hydroxy-estra-1,3,5(10)-trienes of general formula I

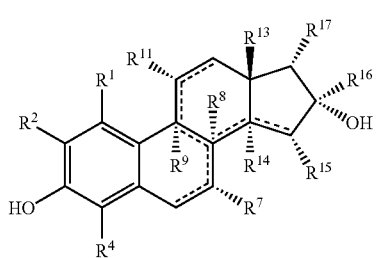

(I)

in which radicals $R^1$ to $R^{17}$, independently of one another, have the following meanings:

$R^1$ means a halogen atom, a hydroxyl group, a methyl group, a trifluoromethyl group, a methoxy group, an ethoxy group or a hydrogen atom;

$R^2$ means a halogen atom, a hydroxyl group, a straight-chain or branched-chain, saturated or unsaturated alkoxy group with up to 6 carbon atoms or a hydrogen atom;

$R^4$ means a halogen atom, a straight-chain or branched-chain, saturated or unsaturated alkyl group with up to 10 carbon atoms, a trifluoromethyl or pentafluoroethyl group, a straight-chain or branched-chain, saturated or unsaturated alkoxy group with up to 6 carbon atoms or a hydrogen atom;

$R^7$ means a halogen atom in α- or β-position, a straight-chain or branched-chain, saturated or unsaturated, optionally partially or completely fluorinated alkyl group with up to 10 carbon atoms in α- or β-position, a straight-chain or branched-chain, saturated or unsaturated alkoxy group with up to 6 carbon atoms, an optionally substituted aryl or heteroaryl radical or a hydrogen atom;

$R^8$ means a hydrogen atom in α- or β-position, a straight-chain or branched-chain, saturated or unsaturated, optionally partially or completely fluorinated alkyl group with up to 10 carbon atoms in α- or β-position, or a cyano group in α- or position;

$R^9$ means a hydrogen atom in α- or β-position, a methyl, ethyl, trifluoromethyl or pentafluoroethyl group in α- or β-position;

$R^{11}$ means a nitrooxy group in α- or β-position, a hydroxyl or mercapto group in α- or β-position, a halogen atom in α- or β-position, a chloromethyl group in α- or β-position, a straight-chain or branched-chain, saturated or unsaturated, optionally partially or completely fluorinated alkyl group with up to 10 carbon atoms in α- or β-position, a straight-chain or branched-chain, saturated or unsaturated alkoxy or alkylthio group with up to 6 carbon atoms, an optionally substituted aryl or heteroaryl radical or a hydrogen atom;

$R^{13}$ means a methyl, ethyl, trifluoromethyl or pentafluoroethyl group in β-position;

and either $R^{14}$ means a straight-chain or branched-chain, saturated or unsaturated, optionally partially or completely fluorinated alkyl group with up to 10 carbon atoms in α- or β-position or a hydrogen atom in α- or β-position and $R^{15}$ means a halogen atom in α- or β-position, a straight-chain or branched-chain, saturated or unsaturated, optionally partially or completely fluorinated alkyl group with up to 10 carbon atoms in α- or β-position that can be interrupted by one or more oxygen atoms, sulfur atoms, sulfoxide or sulfone groups or imino groups $=NR^{15'}$ ($R^{15'}$=hydrogen atom, methyl, ethyl, propyl, i-propyl) or a hydrogen atom or $R^{14}$ and $R^{15}$ together mean a 14α,15α-methylene or 14β,15β-methylene group that is optionally substituted with one or two halogen atoms;

$R^{16}$ means a straight-chain or branched-chain, saturated or unsaturated, optionally partially or completely fluorinated alkyl group with up to 10 carbon atoms in α- or β-position, a trifluoromethyl or pentafluoroethyl group, a cyanomethyl group or a hydrogen atom in α- or β-position;

$R^{17}$ means a halogen atom in α- or β-position, a straight-chain or branched-chain, saturated or unsaturated, optionally partially or completely fluorinated alkyl group with up to 10 carbon atoms in α- or β-position, a hydrogen atom or a hydroxyl group and the dotted lines ------ in rings B, C and D optionally mean one or more double bonds, and the wavy lines mean the arrangement of the respective substituent in α- or β-position, for treatment of estrogen-deficiency-induced diseases and conditions.

According to a variant of the invention, preferably compounds of general formula I are used, in which radicals $R^1$ to $R^{17}$, independently of one another, have the following meanings $R^1$ means a fluorine atom, a hydroxyl group, a methyl group, a trifluoromethyl group, a methoxy group, an ethoxy group or a hydrogen atom;

$R^2$ means a fluorine atom, a hydroxyl group, a methoxy or ethoxy group or a hydrogen atom;

$R^4$ means a fluorine atom, a methyl, ethyl, trifluoromethyl, methoxy or ethoxy group or a hydrogen atom;

$R^7$ means a fluorine atom in α- or β-position, a methyl, ethyl, propyl or i-propyl group in α- or β-position, a trifluoromethyl group in α- or β-position or a hydrogen atom;

$R^8$ means a hydrogen atom in α- or β-position, a methyl or ethyl group in α- or β-position;

$R^9$ means a hydrogen atom in α- or β-position, a methyl, ethyl, trifluoromethyl or pentafluoroethyl group in α- or β-position;

$R^{11}$ means a nitrooxy group in α- or β-position, a hydroxyl group in α- or β-position, a fluorine atom in α- or β-position, a choromethyl group in α- or β-position, a methyl group in α- or β-position, a methoxy group in α- or β-position, a phenyl- or 3-methylthien-2-yl radical in α- or β-position or a hydrogen atom;

$R^{13}$ means a methyl or ethyl group in β-position; and either $R^{14}$ means a hydrogen atom in α- or β-position or a methyl group in α- or β-position and $R^{15}$ means a fluorine atom in α- or β-position, a methyl group in α- or β-position, or a hydrogen atom, or $R^{14}$ and $R^{15}$ together mean a 14α,15α-methylene group or a 14β,15β-methylene group;

$R^{16}$ means a methyl, ethyl, ethinyl, propinyl or trifluoromethyl group;

$R^{17}$ means a fluorine atom in α- or β-position, a methyl group, a hydrogen atom or a hydroxyl group, and the dotted lines ----- in rings B, C and D optionally mean an additional double bond between carbon atoms 9 and 11.

In addition to the above use of the compounds of general formula I, the invention also relates to the compounds of general formula I' themselves. These are the compounds of general formula I excluding the compounds estra-1,3,5(10)-triene-3,16α-diol, estra-1,3,5(10)-triene-3,16β-diol, estra-1,3,5(10),7-tetraene-3,16α-diol as well as estra-1,3,5(10),7-tetraene-3,16β-diol. These last-mentioned compounds are already known; a selective estrogenic action and its use in the context of this invention has not yet been described, however.

16α-Hydroxy-17-methylene estrogens were described as compounds that have an anti-inflammatory action and that are suitable for the therapy of immunological diseases, especially auto-immune diseases (WO 97/08188).

A differentiated action of 16α-hydroxyestrone was already described by Westerlind et al., see above, but not a different action between the brain functions and the vascular system, on the one hand, and on the uterus, on the other.

3,16α-Dihydroxy-estratriene was already described by Stack and Gorski as "estrogen that has a short-term effect" (Stack, Gorski 1985).

Nothing is known to date on a use of this last-mentioned compound as a selective estrogen.

In the compounds of general formulas I and I' as well as in partial structures II and II' that are described below, a fluorine, chlorine, bromine or iodine atom can always stand for a halogen atom; a fluorine atom is preferred in each case.

The alkoxy groups in the compounds of general formulas I and I' as well as in partial structures II and II' that are described below can contain 1 to 6 carbon atoms in each case, whereby methoxy, ethoxy, propoxy, isopropoxy and t-butyloxy groups are preferred.

As representatives of the alkylthio groups, for example, methylthio, ethylthio and trifluoromethylthio groups can be mentioned.

Within the context of this invention, an aryl radical is a phenyl, 1- or 2-naphthyl radical; the phenyl radical is preferred.

Unless expressly indicated, aryl always also includes a heteroaryl radical. Examples of a heteroaryl radical are the 2-, 3- or 4-pyridinyl, the 2- or 3-furyl, the 2- or 3-thienyl, the 2-or 3-pyrrolyl, the 2-, 4- or 5-imidazolyl, the pyrazinyl, the 2-, 4- or 5-pyrimidinyl or 3- or 4-pyridazinyl radical.

As substituents for an aryl or heteroaryl radical, for example, a methyl-, ethyl-, trifluoromethyl-, pentafluoroethyl-, trifluoromethylthio-, methoxy-, ethoxy-, nitro-, cyano-, halogen- (fluorine, chlorine, bromine, iodine), hydroxy-, amino-, mono($C_{1-8}$ alkyl) or di($C_{1-8}$ alkyl)amino, whereby both alkyl groups are identical or different, di(aralkyl)amino, whereby both aralkyl groups are identical or different, can be mentioned.

As representatives of straight-chain or branched-chain alkyl groups with 1–10 carbon atoms, for example, methyl, ethyl, propyl, isopropyl, butyl, isobutyl, tert-butyl, pentyl, isopentyl, neopentyl, heptyl, hexyl, decyl can be mentioned; methyl, ethyl, propyl and isopropyl are preferred.

The alkyl groups can be partially or completely fluorinated or substituted by 1–5 halogen atoms, hydroxy groups or $C_1$–$C_4$ alkoxy groups.

As perfluorinated alkyl groups, for example, trifluoromethyl, pentafluoroethyl and nonafluorobutyl can be mentioned. Representatives of partially fluorinated alkyl groups are, for example, 2,2,2-trifluoroethyl, 5,5,5,4,4-pentafluoropentyl, 9,9,9,8,8,7,7,6,6-nonafluorohexyl, etc.

Monochloromethylene, monofluoromethylene or difluoromethylene can stand for the halogen-substituted 14,15-methylene group.

Other variants of the invention provide one or more conjugated double bonds in rings B, C and D of the estratriene skeleton:

A double bond between C atoms 6 and 7 or between C atoms 7 and 8 or between C atoms 8 and 9 or between C atoms 9 and 11 or between C atoms 8 and 14 or between C atoms 14 and 15 or double bonds between C atoms 6 and 7 and C atoms 8 and 9 or between C atoms 8 and 9 and C atoms 14 and 15 or between C atoms 6 and 7, C atoms 8 and 9 and C atoms 11 and 12 or between C atoms 6 and 7, C atoms 8 and 9 and C atoms 14 and 15 or between C atoms 6 and 7, C atoms 8 and 9, C atoms 11 and 12 and C atoms 14 and 15.

One or both hydroxyl groups at C atoms 3 and 16 can be esterified with an aliphatic, straight-chain or branched-chain, saturated or unsaturated $C_1$–$C_{14}$ mono- or polycarboxylic acid or an aromatic carboxylic acid or with an α- or β-amino acid.

Suitable as such carboxylic acids for esterification are, for example:

Monocarboxylic acids: formic acid, acetic acid, propionic acid, butyric acid, isobutyric acid, valeric acid, isovaleric acid, pivalic acid, lauric acid, myristic acid, acrylic acid, propiolic acid, methacrylic acid, crotonic acid, isocrotonic acid, oleic acid, elaidic acid.

Dicarboxylic acids: oxalic acid, malonic acid, succinic acid, glutaric acid, adipic acid, pimelic acid, suberic acid, azelaic acid, sebacic acid, maleic acid, fumaric acid, muconic acid, citraconic acid, and mesaconic acid.

Aromatic carboxylic acids: benzoic acid, phthalic acid, isophthalic acid, terephthalic acid, naphthoic acid, o-, m- and p-toluic acid, hydratropic acid, atropic acid, cinnamic acid, nicotinic acid, and isonicotinic acid.

As amino acids, the representatives of these classes of substances that are known sufficiently to one skilled in the art are suitable, for example, alanine, β-alanine, arginine, cysteine, cystine, glycine, histidine, leucine, isoleucine, phenylalanine, proline, etc.

The 16-oxy group in the compounds according to the invention and the structural parts that are described below can be both in α-position and in β-position.

A variant of the invention provides that in compounds of general formulas I and I' as well as in the structural parts of formula II'
  $R^7$ means a halogen atom in α- or β-position, a straight-chain or branched-chain, saturated or unsaturated, optionally partially or completely fluorinated alkyl group with up to 10 carbon atoms in α- or β-position, a straight-chain or branched-chain, saturated or unsaturated alkoxy group with up to 6 carbon atoms and/or an optionally substituted aryl or heteroaryl radical and
  $R^1, R^2, R^4, R^8, R^9, R^{11}, R^{14}, R^{15}, R^{16}$ and $R^{17}$ in each case mean a hydrogen atom.

According to another embodiment of the invention, in the compounds of general formulas I and I', and in the structural parts of formula II'
  $R^{11}$ means a nitrooxy group in α- or β-position, a hydroxyl or mercapto group in α- or β-position, a halogen atom in α- or β-position, a chloromethyl group in α- or β-position, a straight-chain or branched-chain, saturated or unsaturated, optionally partially or completely fluorinated alkyl group with up to 10 carbon atoms in α- or β-position, a straight-chain or branched-chain, saturated or unsaturated alkoxy or alkylthio group with up to 6 carbon atoms or an optionally substituted aryl or heteroaryl radical, and
  $R^1, R^2, R^4, R^7, R^8, R^9, R^{14}, R^{15}, R^{16}$ and $R^{17}$ in each case mean a hydrogen atom.

Another configuration of the compounds of general formulas I and I' as well as the structural parts of formula II' provides that
  $R^{15}$ means a halogen atom in α- or β-position or a straight-chain or branched-chain, saturated or unsaturated, optionally partially or completely fluorinated alkyl group with up to 10 carbon atoms in α- or β-position that can be interrupted by one or more oxygen atoms, sulfur atoms, sulfoxide or sulfone groups or imino groups =$NR^{15'}$ ($R^{15'}$=hydrogen atom, methyl, ethyl, propyl, i-propyl), and
  $R^1, R^2, R^4, R^7, R^8, R^9, R^{11}, R^{14}, R^{16}$ and $R^{17}$ in each case mean a hydrogen atom.

In another variant of the compounds of general formulas I and I' according to the invention as well as the structural parts of formula II',
  $R^7$ means a halogen atom in α- or β-position, a straight-chain or branched-chain, saturated or unsaturated, optionally partially or completely fluorinated alkyl group with up to 10 carbon atoms in α- or β-position, a straight-chain or branched-chain, saturated or unsaturated alkoxy group with up to 6 carbon atoms or an optionally substituted aryl or heteroaryl radical, and
  $R^{11}$ means a nitrooxy group in α- or β-position, a hydroxyl- or mercapto group in α- or β-position, a halogen atom in α- or β-position, a chloromethyl group in α- or β-position, a straight-chain or branched-chain, saturated or unsaturated, optionally partially or completely fluorinated alkyl group with up to 10 carbon atoms in α- or β-position, a straight-chain or branched-chain, saturated or unsaturated alkoxy or alkylthio group with up to 6 carbon atoms or an optionally substituted aryl or heteroaryl radical, and
  $R^1, R^2, R^4, R^8, R^9, R^{14}, R^{15}, R^{16}$ and $R^{17}$ in each case mean a hydrogen atom.

In another variant of the compounds of general formulas I and I' according to the invention as well as the structural parts of formula II',
  $R^7$ stands for a halogen atom in α- or β-position, a straight-chain or branched-chain, saturated or unsaturated, optionally partially or completely fluorinated alkyl group with up to 10 carbon atoms in α- or β-position, a straight-chain or branched-chain, saturated or unsaturated alkoxy group with up to 6 carbon atoms or an optionally substituted aryl or heteroaryl radical, and
  $R^{15}$ stands for a halogen atom in α- or β-position or a straight-chain or branched-chain, saturated or unsaturated, optionally partially or completely fluorinated alkyl group with up to 10 carbon atoms in α- or β-position that can be interrupted by one or more oxygen atoms, sulfur atoms, sulfoxide or sulfone groups or imino groups =$NR^{15'}$ ($R^{15'}$=hydrogen atom, methyl, ethyl, propyl, i-propyl), and
  $R^1 R^2, R^4, R^8, R^9, R^{11}, R^{14}, R^{16}$ and $R^{17}$ in each case stand for a hydrogen atom.

According to another embodiment of the compounds of general formulas I and I' according to the invention and the structural parts of formula II',
  $R^{11}$ stands for a nitrooxy group in α- or β-position, a hydroxyl or mercapto group in α- or β-position, a halogen atom in α- or β-position, a chloromethyl group in α- or β-position, a straight-chain or branched-chain, saturated or unsaturated, optionally partially or completely fluorinated alkyl group with up to 10 carbon atoms in α- or β-position, a straight-chain or branched-chain, saturated or unsaturated alkoxy or alkylthio group with up to 6 carbon atoms or an optionally substituted aryl or heteroaryl radical, and
  $R^{15}$ stands for a halogen atom in α- or β-position or a straight-chain or branched-chain, saturated or unsaturated, optionally partially or completely fluorinated alkyl group with up to 10 carbon atoms in α- or β-position that can be interrupted by one or more oxygen atoms, sulfur atoms, sulfoxide or sulfone groups or imino groups =$NR^{15}$ ($R^{15}$=hydrogen atom, methyl, ethyl, propyl, i-propyl), and
  $R^1, R^2, R^4, R^7, R^8, R^9, R^{14}, R^{16}$, and $R^{17}$ in each case stand for a hydrogen atom.

There are also embodiments of the compounds of general formulas I and I' according to the invention as well as the structural parts of formula II', in which
  $R^7$ means a halogen atom in α- or β-position, a straight-chain or branched-chain, saturated or unsaturated, optionally partially or completely fluorinated alkyl group with up to 10 carbon atoms in α- or β-position, a straight-chain or branched-chain, saturated or unsaturated alkoxy group with up to 6 carbon atoms or an optionally substituted aryl or heteroaryl radical,
  $R^{11}$ means a nitrooxy group in α- or β-position, a hydroxyl or mercapto group in α- or β-position, a halogen atom in α- or β-position, a chloromethyl group in α- or β-position, a straight-chain or branched-chain, saturated or unsaturated, optionally partially or completely fluorinated alkyl group with up to 10 carbon atoms in α- or β-position, a straight-chain or branched-chain, saturated or unsaturated alkoxy or alkylthio group with up to 6 carbon atoms or an optionally substituted aryl or heteroaryl radical, $R^{15}$ means a halogen atom in α- or β-position, or a straight-chain or branched-chain, saturated or unsaturated, optionally partially or completely fluorinated alkyl group with up to 10 carbon atoms in α- or β-position that can be interrupted by one or more oxygen atoms, sulfur atoms, sulfoxide or sulfone groups or imino groups =$NR^{15'}$ ($R^{15'}$=hydrogen atom, methyl, ethyl, propyl, i-propyl), and $R^1$, $R^2$, $R^4$, $R^8$, $R^9$, $R^{14}$, $R^{16}$, and $R^{17}$ in each case mean a hydrogen atom.

In the variants of the compounds of general formula I according to the invention that are indicated above as well as the partial structures of general formula II', $R^7$ preferably stands for a fluorine atom in α- or β-position, a methyl, ethyl, propyl or i-propyl group in α- or β-position, a trifluoromethyl group in α- or β-position or a hydrogen atom;

$R^{11}$ preferably stands for a nitrooxy group in α- or position, a hydroxyl group in α- or β-position, a fluorine atom in α- or β-position, a chloromethyl group in α- or β-position, a methyl group in α- or β-position, a methoxy group in α- or β-position, a phenyl or 3-methylthien-2-yl radical in α- or position or a hydrogen atom and $R^{15}$ preferably stands for a fluorine atom in α- or position, a methyl group in α- or β-position or a hydrogen atom.

Preferred according to this invention are the compounds below:

14α,15α-Methylen-estra-1,3,5(10)-triene-3,16α-diol
14β,15β-Methylen-estra-1,3,5(10)-triene-3,16α-diol
14β,15β-Methylen-estra-1,3,5(10),8(9)-tetraene-3,16α-diol,
Estra-1,3,5(10),8(9)-tetraene-3,16α-diol,
Estra-1,3,5(10),8(14)-tetraene-3,16α-diol,
Estra-1,3,5(10),6,8-pentaene-3,16α-diol,
7α-Fluoro-estra-1,3,5(10)-triene-3,16α-diol,
11-Methoxy-estra-1,3,5(10)-triene-3,16α-diol,
7α-Methyl-estra-1,3,5(10)-triene-3,16α-diol
11'-Fluoro-estra-1,3,5(10)-triene-3,16α-diol,
8α-Estra-1,3,5(10)-triene-3,16α-diol
Estra-1,3,5(10)-triene-2,3,16α-triol
17β-Fluoro-estra-1,3,5(10)-triene-3,16α-diol,
18α-Homo-estra-1,3,5(10)-triene-3,16α-diol,
18α-Homo-estra-1,3,5(10),8(9)-tetraene-3,16α-diol,
18α-Homo-14α,15α-methylen-estra-1,3,5(10)-triene-3, 16α-diol,
18α-Homo-14α,15α-methylen-estra-1,3,5(10),8(9)-tetraene-3,16α-diol,
18α-Homo-14α,15α-methylen-estra-1,3,5(10),6,8-pentaene-3,16α-diol.
14α,15α-Methylen-estra-1,3,5(10)-triene-3,16β-diol
14β,15β-Methylen-estra-1,3,5(10)-triene-3,16β-diol
14β,15β-Methylen-estra-1,3,5(10),8(9)-tetraene-3,16β-diol,
Estra-1,3,5(10),8(9)-tetraene-3,16β-diol,
Estra-1,3,5(10),8(14)-tetraene-3,16β-diol,
Estra-1,3,5(10),6,8-pentaene-3,16β-diol,
7α-Fluoro-estra-1,3,5(10)-triene-3,16β-diol,
11β-Methoxy-estra-1,3,5(10)-triene-3,16β-diol,
7α-Methyl-estra-1,3,5(10)-triene-3,16β-diol
11β-Fluoro-estra-1,3,5(10)-triene-3,16β-diol,
8α-Estra-1,3,5(10)-triene-3,16β-diol
Estra-1,3,5(10)-triene-2,3,16β-triol
17β-Fluoro-estra-1,3,5(10)-triene-3,16β-diol,
18α-Homo-estra-1,3,5(10)-triene-3,16β-diol,
18α-Homo-estra-1,3,5(10),8(9)-tetraene-3,16β-diol,
18α-Homo-14α,15α-methylen-estra-1,3,5(10)-triene-3, 16β-diol,
18α-Homo-14α,15α-methylen-estra-1,3,5(10),8(9)-tetraene-3,16β-diol,
18α-Homo-14α,15α-methylen-estra-1,3,5(10),6,8-pentaene-3,16β-diol,
7α-Ethyl-estra-1,3,5(10)-triene-3,16α-diol
7α-Propyl-estra-1,3,5(10)-triene-3,16α-diol
7α-i-Propyl-estra-1,3,5(10)-triene-3,16α-diol
7α-i-Propenyl-estra-1,3,5(10)-triene-3,16α-diol
7α-Phenyl-estra-1,3,5(10)-triene-3,16α-diol
7α-Methoxy-estra-1,3,5(10)-triene-3,16α-diol
7α-Thiomethyl-estra-1,3,5(10)-triene-3,16α-diol
7β-Cyanomethyl-estra-1,3,5(10)-triene-3,16β-diol
7β-Ethyl-estra-1,3,5(10)-triene-3,16≠-diol
7β-Propyl-estra-1,3,5(10)-triene-3,16α-diol
7β-i-Propyl-estra-1,3,5(10)-triene-3,16α-diol
7β-i-Propenyl-estra-1,3,5(10)-triene-3,16α-diol
7β-Phenyl-estra-1,3,5(10)-triene-3,16α-diol
7β-Methoxy-estra-1,3,5 (10)-triene-3,16α-diol
7β-Thiomethyl-estra-1,3,5(10)-triene-3,16α-diol
7β-Cyanomethyl-estra-1,3,5(10)-triene-3,16α-diol
7α-Ethyl-estra-1,3,5(10)-triene-3,16β-diol
7α-Propyl-estra-1,3,5(10)-triene-3,16β-diol
7α-i-Propyl-estra-1,3,5(10)-triene-3,16β-diol
7α-i-Propenyl-estra-1,3,5(10)-triene-3,16β-diol
7α-Phenyl-estra-1,3,5(10)-triene-3,16β-diol
7α-Methoxy-estra-1,3,5(10)-triene-3,16β-diol
7α-Thiomethyl-estra-1,3,5(10)-triene-3,16β-diol
7α-Cyanomethyl-estra-1,3,5(10)-triene-3,16β-diol
7β-Ethyl-estra-1,3,5(10)-triene-3,16β-diol
7β-Propyl-estra-1,3,5(10)-triene-3,16β-diol
7β-i-Propyl-estra-1,3,5(10)-triene-3,16β-diol
7β-i-Propenyl-estra-1,3,5(10)-triene-3,16β-diol
7β-Phenyl-estra-1,3,5(10)-triene-3,16β-diol
7β-Methoxy-estra-1,3,5(10)-triene-3,16β-diol
7β-Thiomethyl-estra-1,3,5(10)-triene-3,16β-diol
7β-Cyanomethyl-estra-1,3,5(10)-triene-3,16β-diol
15α-Methyl-estra-1,3,5(10)-triene-3,16α-diol
15α-Ethyl-estra-1,3,5(10)-triene-3,16α-diol
15α-Propyl-estra-1,3,5(10)-triene-3,16α-diol
15α-Allyl-estra-1,3,5(10)-triene-3,16α-diol
15α-i-Propyl-estra-1,3,5(10)-triene-3,16α-diol
15α-i-Propenyl-estra-1,3,5(10)-triene-3,16α-diol
15α-Methoxy-estra-1,3,5(10)-triene-3,16α-diol
15α-Thiomethyl-estra-1,3,5(10)-triene-3,16α-diol
15α-Methyl-estra-1,3,5(10)-triene-3,16β-diol
15α-Ethyl-estra-1,3,5(10)-triene-3,16β-diol
15α-Propyl-estra-1,3,5(10)-triene-3,16β-diol
15α-Allyl-estra-1,3,5(10)-triene-3,16β-diol
15α-i-Propyl-estra-1,3,5(10)-triene-3,16β-diol
15α-i-Propenyl-estra-1,3,5(10)-triene-3,16β-diol
15α-Methoxy-estra-1,3,5(10)-triene-3,16β-diol
15α-Thiomethyl-estra-1,3,5(10)-triene-3,16β-diol
15β-Methyl-estra-1,3,5(10)-triene-3,16α-diol
15β-Ethyl-estra-1,3,5(10)-triene-3,16α-diol
15β-Propyl-estra-1,3,5(10)-triene-3,16α-diol
15β-Allyl-estra-1,3,5(10)-triene-3,16α-diol
15β-i-Propyl-estra-1,3,5(10)-triene-3,16α-diol
15β-i-Propenyl-estra-1,3,5(10)-triene-3,16α-diol
15β-Methoxy-estra-1,3,5(10)-triene-3,16α-diol
15β-Thiomethyl-estra-1,3,5(10)-triene-3,16α-diol
15β-Methyl-estra-1,3,5(10)-triene-3,16β-diol
15β-Ethyl-estra-1,3,5(10)-triene-3,16β-diol
15β-Propyl-estra-1,3,5(10)-triene-3,16β-diol
15β-Allyl-estra-1,3,5(10)-triene-3,16β-diol 15β-i-Propyl-estra-1,3,5(10)-triene-3,16β-diol
15β-i-Propenyl-estra-1,3,5(10)-triene-3,16β-diol
15β-Methoxy-estra-1,3,5(10)-triene-3,16β-diol
15β-Thiomethyl-estra-1,3,5(10)-triene-3,16β-diol
7α-Trifluoromethyl-11β-fluoro-estra-1,3,5(10)-triene-3,16α-diol
7α-Pentafluoroethyl-11β-fluoro-estra-1,3,5(10)-triene-3,16α-diol
7α-Ethyl-11β-fluoro-estra-1,3,5(10)-triene-3,16α-diol
7α-Propyl-11β-fluoro-estra-1,3,5(10)-triene-3,16α-diol
7α-i-Propyl-11β-fluoro-estra-1,3,5(10)-triene-3,16α-diol
7α-i-Propenyl-11β-fluoro-estra-1,3,5(10)-triene-3,16α-diol
7α-Phenyl-11α-Fluoro-estra-1,3,5(10)-triene-3,16α-diol
7α-Methoxy-11β-fluoro-estra-1,3,5(10)-triene-3,16α-diol
7α-Thiomethyl-11β-fluoro-estra-1,3,5(10)-triene-3,16α-diol
7α-Cyanomethyl-11β-fluoro-estra-1,3,5(10)-triene-3,16α-diol
7β-Ethyl-11β-fluoro-estra-1,3,5(10)-triene-3,16α-diol
7β-Propyl-11β-fluoro-estra-1,3,5(10)-triene-3,16α-diol
7β-i-Propyl-11β-fluoro-estra-1,3,5(10)-triene-3,16α-diol
7β-i-Propenyl-11β-fluoro-estra-1,3,5(10)-triene-3,16α-diol
7β-Phenyl-11β-fluoro-estra-1,3,5(10)-triene-3,16α-diol
7β-Methoxy-11β-fluoro-estra-1,3,5(10)-triene-3,16α-diol
7β-Thiomethyl-11β-fluoro-estra-1,3,5(10)-triene-3,16α-diol
7α-Cyanomethyl-11β-fluoro-estra-1,3,5(10)-triene-3,16α-diol
7α-Ethyl-11β-fluoro-estra-1,3,5(10)-triene-3,16β-diol
7α-Propyl-11β-fluoro-estra-1,3,5(10)-triene-3,16β-diol
7α-i-Propyl-11β-fluoro-estra-1,3,5(10)-triene-3,16β-diol
7α-i-Propenyl-11β-fluoro-estra-1,3,5(10)-triene-3,16β-diol
7α-Phenyl-11β-fluoro-estra-1,3,5(10)-triene-3,16β-diol
7α-Methoxy-11β-fluoro-estra-1,3,5(10)-triene-3,16β-diol
7α-Thiomethyl-11β-fluoro-estra-1,3,5(10)-triene-3,16β-diol
7α-Cyanomethyl-11β-fluoro-estra-1,3,5(10)-triene-3,16β-diol
7β-Ethyl-11β-fluoro-estra-1,3,5(10)-triene-3,16β-diol
7β-Propyl-11β-fluoro-estra-1,3,5(10)-triene-3,16β-diol
7β-i-Propyl-11β-fluoro-estra-1,3,5(10)-triene-3,16β-diol
7β-i-Propenyl-11β-fluoro-estra-1,3,5(10)-triene-3,16β-diol
7β-Phenyl-11β-fluoro-estra-1,3,5(10)-triene-3,16β-diol
7β-Methoxy-11β-fluoro-estra-1,3,5(10)-triene-3,16β-diol
7β-Thiomethyl-11β-fluoro-estra-1,3,5(10)-triene-3,16β-diol
7β-Cyanomethyl-11β-fluoro-estra-1,3,5(10)-triene-3,16β-diol
15α-Methyl-11β-fluoro-estra-1,3,5(10)-triene-3,16α-diol
15α-Ethyl-11β-fluoro-estra-1,3,5(10)-triene-3,16α-diol
15α-Propyl-11β-fluoro-estra-1,3,5(10)-triene-3,16α-diol
15α-Allyl-11β-fluoro-estra-1,3,5(10)-triene-3,16α-diol
15α-i-Propyl-11β-fluoro-estra-1,3,5(10)-triene-3,16α-diol
15α-i-Propenyl-11β-fluoro-estra-1,3,5(10)-triene-3,16α-diol
15α-Methoxy-11β-fluoro-estra-1,3,5(10)-triene-3,16α-diol
15α-Thiomethyl-11β-fluoro-estra-1,3,5(10)-triene-3,16α-diol
15α-Methyl-11β-fluoro-estra-1,3,5(10)-triene-3,16β-diol
15α-Ethyl-11β-fluoro-estra-1,3,5(10)-triene-3,16β-diol
15α-Propyl-11β-fluoro-estra-1,3,5(10)-triene-3,16β-diol
15α-Allyl-11β-fluoro-estra-1,3,5(10)-triene-3,16β-diol
15α-i-Propyl-11β-fluoro-estra-1,3,5(10)-triene-3,16α-diol
15α-i-Propenyl-11β-fluoro-estra-1,3,5(10)-triene-3,16β-diol
15α-Methoxy-11β-fluoro-estra-1,3,5(10)-triene-3,16β-diol
15α-Thiomethyl-11β-fluoro-estra-1,3,5(10)-triene-3,16β-diol
15β-Methyl-11β-fluoro-estra-1,3,5(10)-triene-3,16α-diol
15β-Ethyl-11β-fluoro-estra-1,3,5(10)-triene-3,16α-diol
15β-Propyl-11β-fluoro-estra-1,3,5(10)-triene-3,16α-diol
15β-Allyl-11β-fluoro-estra-1,3,5(10)-triene-3,16α-diol
15β-i-Propyl-11β-fluoro-estra-1,3,5(10)-triene-3,16α-diol
15β-i-Propenyl-11β-fluoro-estra-1,3,5(10)-triene-3,16α-diol
15β-Methoxy-11β-fluoro-estra-1,3,5(10)-triene-3,16α-diol
15β-Thiomethyl-11β-fluoro-estra-1,3,5(10)-triene-3,16α-diol
15β-Methyl-11β-fluoro-estra-1,3,5(10)-triene-3,16β-diol
15β-Ethyl-11β-fluoro-estra-1,3,5(10)-triene-3,16β-diol
15β-Propyl-11β-fluoro-estra-1,3,5(10)-triene-3,16β-diol
15β-Allyl-11β-fluoro-estra-1,3,5(10)-triene-3,16β-diol
15β-i-Propyl-11β-fluoro-estra-1,3,5(10)-triene-3,16β-diol
15β-i-Propenyl-11β-fluoro-estra-1,3,5(10)-triene-3,16β-diol
15β-Methoxy-11β-fluoro-estra-1,3,5(10)-triene-3,16β-diol
15β-Thiomethyl-11β-fluoro-estra-1,3,5(10)-triene-3,16β-diol
14α,15α-Methylene-7α-phenyl-estra-1,3,5(10)-triene-3,16α-diol
14β,15β-Methylene-7α-phenyl-estra-1,3,5(10)-triene-3,16α-diol
14β,15β-Methylene-7α-phenyl-estra-1,3,5(10),8(9)-tetraene-3,16α-diol,
7α-Phenyl-estra-1,3,5(10),8(9)-tetraene-3,16α-diol,
7α-Phenyl-estra-1,3,5(10),8(14)-tetraene-3,16α-diol,
7α-Phenyl-estra-1,3,5(10),6,8-pentaene-3,16α-diol,
11β-Methoxy-7α-phenyl-estra-1,3,5(10)-triene-3,16α-diol,
11β-Fluoro-7α-phenyl-estra-1,3,5(10)-triene-3,16α-diol,
7α-Phenyl-8α-estra-1,3,5(10)-triene-3,16α-diol
7α-Phenyl-estra-1,3,5(10)-triene-2,3,16α-triol
17β-Fluoro-7α-phenyl-estra-1,3,5(10)-triene-3,16α-diol,
18α-Homo-7α-phenyl-estra-1,3,5(10)-triene-3,16α-diol,
18α-Homo-7α-phenyl-estra-1,3,5(10),8(9)-tetraene-3,16α-diol,
18α-Homo-14α,15α-methylene-7α-phenyl-estra-1,3,5(10)-triene-3,16α-diol,
18α-Homo-14α,15α-methylene-7α-phenyl-estra-1,3,5(10),8(9)-tetraene-3,16α-diol,
18α-Homo-14α,15α-methylene-7α-phenyl-estra-1,3,5(10),6,8-pentaene-3,16α-diol,
14α,15α-Methylene-7α-phenyl-estra-1,3,5(10)-triene-3,16β-diol
14β,15β-Methylene-7α-phenyl-estra-1,3,5(10)-triene-3,16β-diol
14β,15β-Methylene-7α-phenyl-estra-1,3,5(10),8(9)-tetraene-3,16β-diol,
7α-Phenyl-estra-1,3,5(10),8(9)-tetraene-3,16β-diol,
7α-Phenyl-estra-1,3,5(10),8(14)-tetraene-3,16β-diol,
7α-Phenyl-estra-1,3,5(10),6,8-pentaene-3,16β-diol,
11β-Methoxy-7α-phenyl-estra-1,3,5(10)-triene-3,16α-diol,
11β-Fluoro-7α-phenyl-estra-1,3,5(10)-triene-3,16β-diol,
7α-Phenyl-8α-estra-1,3,5(10)-triene-3,16β-diol
7α-Phenyl-estra-1,3,5(10)-triene-2,3,16α-triol
17β-Fluoro-7α-phenyl-estra-1,3,5(10)-triene-3,16β-diol,
18α-Homo-7α-phenyl-estra-1,3,5(10)-triene-3,16β-diol,
18α-Homo-7α-phenyl-estra-1,3,5(10),8(9)-tetraene-3,16β-diol,
18α-Homo-14α,15α-methylene-7α-phenyl-estra-1,3,5(10)-triene-3,16%-diol,
18α-Homo-14α,15α-methylene-7α-phenyl-estra-1,3,5(10),8(9)-tetraene-3,16β-diol,
18α-Homo-14α,15α-methylene-7α-phenyl-estra-1,3,5(10),6,8-pentaene-3,16β-diol,
15α-Methyl-7α-phenyl-estra-1,3,5(10)-triene-3,16-diol 15α-Ethyl-7α-phenyl-estra-1,3,5(10)-triene-3,16α-diol
15α-Propyl-7α-phenyl-estra-1,3,5(10)-triene-3,16α-diol
15α-Allyl-7α-phenyl-estra-1,3,5(10)-triene-3,16α-diol
15α-i-Propyl-7α-phenyl-estra-1,3,5(10)-triene-3,16α-diol
15α-i-Propenyl-7α-phenyl-estra-1,3,5(10)-triene-3,16α-diol
15α-Methoxy-7α-phenyl-estra-1,3,5(10)-triene-3,16α-diol
15α-Thiomethyl-7α-phenyl-estra-1,3,5(10)-triene-3,16α-diol
15α-Methyl-7α-phenyl-estra-1,3,5(10)-triene-3,16β-diol
15α-Ethyl-7α-phenyl-estra-1,3,5(10)-triene-3,16β-diol
15α-Propyl-7α-phenyl-estra-1,3,5(10)-triene-3,16β-diol
15α-Allyl-7 μL-phenyl-estra-1,3,5(10)-triene-3,16β-diol
15α-i-Propyl-7α-phenyl-estra-1,3,5(10)-triene-3,16β-diol
15α-i-Propenyl-7α-phenyl-estra-1,3,5(10)-triene-3,16β-diol
15α-Methoxy-7α-phenyl-estra-1,3,5(10)-triene-3,16β-diol
15α-Thiomethyl-7α-phenyl-estra-1,3,5(10)-triene-3,16β-diol
15β-Methyl-7α-phenyl-estra-1,3,5(10)-triene-3,16α-diol
15β-Ethyl-7α-phenyl-estra-1,3,5(10)-triene-3,16α-diol
15β-Propyl-7α-phenyl-estra-1,3,5(10)-triene-3,16α-diol
15β-Allyl-7α-phenyl-estra-1,3,5(10)-triene-3,16α-diol
15β-i-Propyl-7α-phenyl-estra-1,3,5(10)-triene-3,16α-diol
15β-i-Propenyl-7α-phenyl-estra-1,3,5(10)-triene-3,16α-diol
15β-Methoxy-7α-phenyl-estra-1,3,5(10)-triene-3,16α-diol
15β-Thiomethyl-7α-phenyl-estra-1,3,5(10)-triene-3,16α-diol
15'-Methyl-7α-phenyl-estra-1,3,5(10)-triene-3,16β-diol
15β-Ethyl-7α-phenyl-estra-1,3,5(10)-triene-3,16β-diol
15β-Propyl-7α-phenyl-estra-1,3,5(10)-triene-3,16β-diol
15β-Allyl-7α-phenyl-estra-1,3,5(10)-triene-3,16β-diol
15β-i-Propyl-7α-phenyl-estra-1,3,5(10)-triene-3,16β-diol
15β-i-Propenyl-7α-phenyl-estra-1,3,5(10)-triene-3,16β-diol
15β-Methoxy-7α-phenyl-estra-1,3,5(10)-triene-3,16β-diol
15β-Thiomethyl-7α-phenyl-estra-1,3,5(10)-triene-3,16β-diol
15α-Methyl-11β-fluoro-7α-phenyl-estra-1,3,5(10)-triene-3,16α-diol
15α-Ethyl-11β-fluoro-7α-phenyl-estra-1,3,5(10)-triene-3,16α-diol
15α-Propyl-11β-fluoro-7α-phenyl-estra-1,3,5(10)-triene-3,16α-diol
15α-Allyl-11β-fluoro-7α-phenyl-estra-1,3,5(10)-triene-3,16α-diol
15α-i-Propyl-11β-fluoro-7α-phenyl-estra-1,3,5(10)-triene-3,16α-diol
15α-i-Propenyl-11β-fluoro-7α-phenyl-estra-1,3,5(10)-triene-3,16α-diol
15α-Methoxy-11β-fluoro-7α-phenyl-estra-1,3,5(10)-triene-3,16α-diol
15α-Thiomethyl-11β-fluoro-7α-phenyl-estra-1,3,5(10)-triene-3,16α-diol
15α-Methyl-11β-fluoro-7α-phenyl-estra-1,3,5(10)-triene-3,16β-diol
15α-Ethyl-11β-fluoro-7α-phenyl-estra-1,3,5(10)-triene-3,16β-diol
15α-Propyl-11β-fluoro-7α-phenyl-estra-1,3,5(10)-triene-3,16β-diol
15α-Allyl-11β-fluoro-7α-phenyl-estra-1,3,5(10)-triene-3,16β-diol
15α-i-Propyl-11β-fluoro-7α-phenyl-estra-1,3,5(10)-triene-3,16β-diol
15α-i-Propenyl-11β-fluoro-7α-phenyl-estra-1,3,5(10)-triene-3,16β-diol
15α-Methoxy-11β-fluoro-7α-phenyl-estra-1,3,5(10)-triene-3,16β-diol
15α-Thiomethyl-11β-fluoro-7α-phenyl-estra-1,3,5(10)-triene-3,16β-diol
15β-Methyl-11β-fluoro-7α-phenyl-estra-1,3,5(10)-triene-3,16α-diol
15β-Ethyl-11β-fluoro-7α-phenyl-estra-1,3,5(10)-triene-3,16α-diol
15β-Propyl-11β-fluoro-7α-phenyl-estra-1,3,5(10)-triene-3,16α-diol
15β-Allyl-11β-fluoro-7α-phenyl-estra-1,3,5(10)-triene-3,16α-diol
15β-i-Propyl-11β-fluoro-7α-phenyl-estra-1,3,5(10)-triene-3,16α-diol
15β-i-Propenyl-11β-fluoro-7α-phenyl-estra-1,3,5(10)-triene-3,16α-diol
15β-Methoxy-11β-fluoro-7α-phenyl-estra-1,3,5(10)-triene-3,16α-diol
15β-Thiomethyl-11β-fluoro-7α-phenyl-estra-1,3,5(10)-triene-3,16α-diol
15β-Methyl-11β-fluoro-7α-phenyl-estra-1,3,5(10)-triene-3,16β-diol
15β-Ethyl-11β-fluoro-7α-phenyl-estra-1,3,5(10)-triene-3,16β-diol
15β-Propyl-11β-fluoro-7α-phenyl-estra-1,3,5(10)-triene-3,16β-diol
15β-Allyl-11β-fluoro-7α-phenyl-estra-1,3,5(10)-triene-3,16β-diol
15β-i-Propyl-11β-fluoro-7α-phenyl-estra-1,3,5(10)-triene-3,16β-diol
15β-i-Propenyl-11β-fluoro-7α-phenyl-estra-1,3,5(10)-triene-3,16β-diol
15β-Methoxy-11β-fluoro-7α-phenyl-estra-1,3,5(10)-triene-3,16β-diol
15β-Thiomethyl-11β-fluoro-7α-phenyl-estra-1,3,5(10)-triene-3,16β-diol
11β-[2-(3-Methylthien)-yl)-estra-1,3,5(10)-triene-3,16α-diol
11β-[2-(3-Methylthien)-yl)-estra-1,3,5(10)-triene-3,16β-diol and of the latter in turn especially the compounds
7α-Fluoro-estra-1,3,5(10)-triene-3,16α-diol,
7α-Methyl-estra-1,3,5(10)-triene-3,16β-diol
7α-Methyl-estra-1,3,5(10)-triene-3,16α-diol
18α-Homo-estra-1,3,5(10)-triene-3,16α-diol.

Another aspect of this invention relates to the use of the structural part of formula II

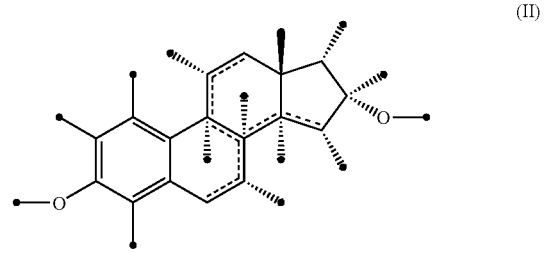

as a component of the total structure of compounds that have a dissociation in favor of their estrogenic action on bone rather than the uterus.

The possible substituents in carbon atoms 7, 8, 9, 11, 13, 14, 15 and 17 can be respectively in α- or β-position. The dotted lines ----- in rings B, C and D stand for one or more possible double bonds between the corresponding carbon atoms.

This invention preferably relates to those structural parts of general formula II'

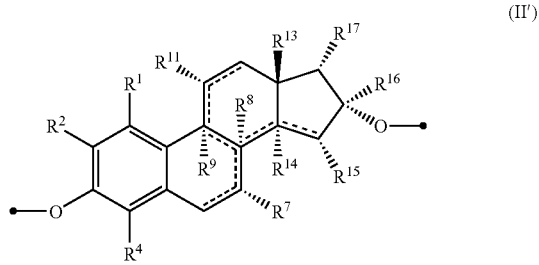

(II')

in which radicals R$^{1'}$ to R$^{17'}$, independently of one another, have the following meanings R$^{1'}$ means a halogen atom, a hydroxyl group, a methyl group, a trifluoromethyl group, a methoxy group, an ethoxy group or a hydrogen atom;

R$^{2'}$ means a halogen atom, a hydroxyl group, a straight-chain or branched-chain, saturated or unsaturated alkoxy group with up to 6 carbon atoms or a hydrogen atom;

R$^{4'}$ means a halogen atom, a straight-chain or branched-chain, saturated or unsaturated alkyl group with up to 10 carbon atoms, a trifluoromethyl or pentafluoroethyl group, a straight-chain or branched-chain, saturated or unsaturated alkoxy group with up to 6 carbon atoms or a hydrogen atom;

R$^{7'}$ means a halogen atom in α- or β-position, a straight-chain or branched-chain, saturated or unsaturated, optionally partially or completely fluorinated alkyl group with up to 10 carbon atoms in α- or β-position, a straight-chain or branched-chain, saturated or unsaturated alkoxy group with up to 6 carbon atoms, an optionally substituted aryl or heteroaryl radical or a hydrogen atom;

R$^{8'}$ means a hydrogen atom in α- or β-position, a straight-chain or branched-chain, saturated or unsaturated, optionally partially or completely fluorinated alkyl group with up to 10 carbon atoms in α- or β-position or a cyano group in α- or β-position;

R$^{9'}$ means a hydrogen atom in α- or β-position, a methyl, ethyl, trifluoromethyl or pentafluoroethyl group in α- or β-position;

R$^{11'}$ means a nitrooxy group in α- or β-position, a hydroxyl or mercapto group in α- or β-position, a halogen atom in α- or β-position, a chloromethyl group in α- or β-position, a straight-chain or branched-chain, saturated or unsaturated, optionally partially or completely fluorinated alkyl group with up to 10 carbon atoms in α- or β-position, a straight-chain or branched-chain, saturated or unsaturated alkoxy or alkylthio group with up to 6 carbon atoms, an optionally substituted aryl or heteroaryl radical or a hydrogen atom;

R$^{13'}$ means a methyl, ethyl, trifluoromethyl or pentafluoroethyl group in β-position;

and either

R$^{14'}$ means a straight-chain or branched-chain, saturated or unsaturated, optionally partially or completely fluorinated alkyl group with up to 10 carbon atoms in α- or β-position or a hydrogen atom in α- or position and R$^{15'}$ means a halogen atom in α- or β-position, a straight-chain or branched-chain, saturated or unsaturated, optionally partially or completely fluorinated alkyl group with up to 10 carbon atoms in α- or β-position that can be interrupted by one or more oxygen atoms, sulfur atoms, sulfoxide or sulfone groups or imino groups =NR$^{15}$ (R$^{15'}$=hydrogen atom, methyl, ethyl, propyl, i-propyl) or a hydrogen atom or R$^{14'}$ and R$^{15'}$ together mean a 14α,15α-methylene group or a 14β,15β-methylene group that is optionally substituted with one or two halogen atoms;

R$^{16'}$ means a straight-chain or branched-chain, saturated or unsaturated, optionally partially or completely fluorinated alkyl group with up to 10 carbon atoms in α- or β-position, a trifluoromethyl or pentafluoroethyl group, a cyanomethyl group or a hydrogen atom in α- or β-position;

R$^{17'}$ means a halogen atom in α- or β-position, a straight-chain or branched-chain, saturated or unsaturated, optionally partially or completely fluorinated alkyl group with up to 10 carbon atoms in α- or β-position, a hydrogen atom or a hydroxyl group, and the dotted lines ---- in rings B, C and D optionally mean one or more double bonds, and the wavy lines mean the arrangement of the respective substituent in α- or β-position.

In this patent application, novel structures for selective estrogens are described, which have in vitro dissociation with respect to binding to estrogen receptor preparations of rat prostates and rat uteri and which have in vivo dissociation with respect to bone action rather than uterus action: the substances act in a bone-protective manner over a wide dose range without stimulating the uterus. In the same dose range, their liver action is small. In addition, the substances exert estrogen-like action on the vascular system and brain functions.

The invention also relates to pharmaceutical preparations that contain at least one compound of general formula I (or physiologically compatible addition salts with organic and inorganic acids of them) and the use of these compounds for the production of pharmaceutical agents, especially for the indications below.

The compounds can be used for the following indications both after oral and parenteral administration.

The novel selective estrogens that are described in this patent can be used as individual components in pharmaceutical preparations or in combination especially with antiestrogens or gestagens. Especially preferred is the combination of selective estrogens with ERα-selective antiestrogens, or with antiestrogens that are peripherally-selectively active, i.e., that do not pass through the blood-brain barriers.

The substances and the pharmaceutical agents that contain them are especially suitable for the treatment of peri- and postmenopausal symptoms, especially hot flashes, sleep disturbances, irritability, mood swings, incontinence, vaginal atrophy, and hormone-deficiency-induced emotional diseases. The substances for hormone substitution and therapy of hormone-deficiency-induced symptoms in the case of surgical, medicinal or ovarian dysfunction that is caused in some other way are also suitable. Prevention of bone mass loss in postmenopausal women, in women who have undergone hysterectomies or in women who were treated with LHRH agonists or LHRH antagonists is also part of this.

The compounds are also suitable for alleviating symptoms of male menopause and female menopause, i.e., for male and female hormone replacement therapy (HRT), specifically both for prevention and for treatment, in addition for treatment of symptoms that are accompanied by a dysmenorrhea as well as for treatment of acne.

In addition, the substances can be used for prophylaxis against hormone-deficiency-induced bone mass loss and osteoporosis, for prevention of cardiovascular diseases, especially vascular diseases such as arteriosclerosis, for prevention of the proliferation of arterial smooth muscle cells, for treatment of primary pulmonary high blood pressure and for prevention of hormone-deficiency-induced neurodegenerative diseases, such as Alzheimer's disease, as well as hormone-deficiency-induced impairment of memory and learning capacity.

In addition, the substances can be used for treatment of inflammatory diseases and diseases of the immune system, especially auto-immune diseases, such as, e.g., rheumatoid arthritis.

In addition, the compounds can be used for the treatment of male fertility disorders and prostatic diseases.

The compounds can also be used in combination with the natural vitamin D3 or with calcitriol analogues for bone formation or as supporting therapies to therapies that cause bone mass loss (for example, therapy with glucocorticoids, chemotherapy).

Finally, the compounds of general formula I can be used in connection with progesterone receptor antagonists, specifically especially for use in hormone replacement therapy and for treatment of gynecological disorders.

A therapeutic product that contains an estrogen and a pure antiestrogen for simultaneous, sequential or separate use for the selective estrogen therapy of perimenopausal or postmenopausal conditions is already described in EP-A 0 346 014.

The amount of a compound of general formula I that is to be administered varies within a wide range and can cover any effective amount. On the basis of the condition that is to be treated and the type of administration, the amount of the compound that is administered can be 0.01 µg/kg–10 mg/kg of body weight, preferably 0.04 µg/kg–1 mg/kg of body weight, per day.

In humans, this corresponds to a dose of 0.8 µg to 800 mg, preferably 3.2 µg to 80 mg, daily.

According to the invention, a dosage unit contains 1.6 µg to 200 mg of one or more compounds of general formula I.

The compounds according to the invention and the acid addition salts are suitable for the production of pharmaceutical compositions and preparations. The pharmaceutical compositions or pharmaceutical agents contain as active ingredient one or more of the compounds according to the invention or their acid addition salts, optionally mixed with other pharmacologically or pharmaceutically active substances. The production of the pharmaceutical agents is carried out in a known way, whereby the known and commonly used pharmaceutical adjuvants as well as other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), page 918 ff., issued by Czetsch-Lindenwald, Hilfsstoffe für Pharmazie und angrenzende Gebiete [Adjuvants for Pharmaceutics and Related Fields]; Pharm. Ind., Issue 2, 1961, p. 72 and ff.: Dr. H. P. Fiedler, Lexikon der Hilfsstoffe für Pharmazie, Kosmetik und angrenzende Gebiete [Dictionary of Adjuvants for Pharmaceutics, Cosmetics and Related Fields], Cantor KG, Aulendorf in Wurttemberg 1971.

The compounds can be administered orally or parenterally, for example intraperitoneally, intramuscularly, subcutaneously or percutaneously. The compounds can also be implanted in the tissue.

For oral administration, capsules, pills, tablets, coated tablets, etc., are suitable. In addition to the active ingredient, the dosage units can contain a pharmaceutically compatible vehicle, such as, for example, starch, sugar, sorbitol, gelatin, lubricant, silicic acid, talc, etc.

For parenteral administration, the active ingredients can be dissolved or suspended in a physiologically compatible diluent. As diluents, very often oils with or without the addition of a solubilizer, a surfactant, a suspending agent or an emulsifying agent are used. Examples of oils that are used are olive oil, peanut oil, cottonseed oil, soybean oil, castor oil and sesame oil.

The compounds can also be used in the form of a depot injection or an implant preparation, which can be formulated so that a delayed release of active ingredient is made possible.

As inert materials, implants can contain, for example, biodegradable polymers, or synthetic silicones such as, for example, silicone rubber. In addition, for percutaneous administration, the active ingredients can be added to, for example, a patch.

For the production of intravaginal systems (e.g., vaginal rings) or intrauterine systems (e.g., pessaries, coils, IUDs, Mirena®) that are loaded with active compounds of general formula I for local administration, various polymers are suitable, such as, for example, silicone polymers, ethylene vinyl acetate, polyethylene or polypropylene.

To achieve better bio-availability of the active ingredient, the compounds can also be formulated as cyclodextrin clathrates. For this purpose, the compounds are reacted with α-, β-, or γ-cyclodextrin or derivatives of the latter (PCT/EP95/02656).

According to the invention, the compounds of general formula I can also be encapsulated with liposomes.

Methodology

Estrogen Receptor Binding Studies

The binding affinity of the new selective estrogens was tested in competitive experiments with use of 3H-estradiol as a ligand to estrogen receptor preparations of rat prostates and rat uteri. The preparation of prostate cytosol and the estrogen receptor test with prostate cytosol was carried out as described by Testas et al. (1981) (Testas, J. et al., 1981, Endocrinology 109: 1287–1289).

The preparation of rat uterus cytosol, as well as the receptor test with the ER-containing cytosol were basically performed as described by Stack and Gorski, 1985 (Stack, Gorski 1985, Endocrinology 117, 2024–2032) with some modification as described in Fuhrmann et al. (1995) (Fuhrmann, U. et al. 1995, Contraception 51: 45–52).

The substances that are described in this patent have higher binding affinity to the estrogen receptor of rat prostates than to estrogen receptors of rat uteri. In this case, it is assumed that ERβ predominates in the rat prostates over ERα, and ERα predominates in rat uteri over ERβ. Table 1 shows that the ratio of the binding to prostate and uterus receptors qualitatively coincides with the quotient of relative binding affinity (RBA) to human ERβ and ERα of rats (according to Kuiper et al. (1996), Endocrinology 138: 863–870) (Table 1).

Some studies with human estrogen receptors α and β, which were produced by means of the Baculovirus/SF-9 expression system, confirm the agreement of the 'RBA prostate-ER/RBA uterus-ER' ratio with the 'RBA ERβ/RBA ERα' quotient (Table 2).

In addition, the predictability of the 'prostate-ER versus the uterus-ER test system' was confirmed with respect to tissue-selective action by in vivo studies. Substances with a preference for prostate-ER are dissociated in vivo with respect to bone and uterus action in favor of action on bones.

Bone Studies

Three-month-old female rats are ovariectomized and treated once daily with the test compound immediately after the operation for 28 days. The administration is carried out subcutaneously in arachis oil/ethanol. The animals are sacrificed on the day after the last administration, and tibia as well as uteri are removed. The uteri are weighed, fixed and worked up for histological studies. The determination of bone density is carried out ex vivo on prepared long bones by means of pQCT (quantitative computer tomography). The measurements are made at a distance of 4–6 mm from the ball of the joint of the proximal tibia.

The ovariectomy reduces the density of the trabecular bone in the measured area by about 400 mg of $Ca^{2+}/cm^3$ to about 300 mg of $Ca^{2+}/cm^3$. By treatment with a compound of general formula I according to this invention, the degradation of the bone density is prevented or inhibited. The bone density in the proximal tibia was measured.

Table 3 shows the results for the compound estra-1,3,5 (10)-triene-3,16α-diol that is to be used according to the invention. In accordance with the higher binding affinity to ERβ than to ERα, [ERα (RBA)/ERα (RBA) 6] shows a higher binding affinity to the estrogen receptor of rat prostates [ER(RBA)=50] than to the estrogen receptor of rat uteri [ER(RBA)=9]. Estra-1,3,5(10)-triene-3,16α-diol reflects this in vivo in the greatly different amounts, which produce a 50% bone protection [3 μg/animal] or a 50% uterus stimulation [30 μg/animal], relative to the bone mass loss, which can be measured in ovariectomized, untreated female rats 28 days after the ovariectomy unlike in intact animals that are subjected to sham operations.

The vascular action of the estrogens according to the invention is determined in the model of the ApoE-knockout mouse, as described by R. Elhage et al., 1997, (Elhage, R. et al. 1997, Arteriosclerosis, Thrombosis and Vascular Biology 17: 2679–2684).

To detect the action of estrogens in the brain function, the oxytocin receptor mRNA expression is used as a surrogate parameter (Hrabovszky, E. et al. 1998, Endocrinology 1339: 2600–2604). Ovariectomized rats are treated for 7 days with the test substance or vehicle (administration: subcutaneous or oral, six times daily). On day 7 after the first administration, the animals are decapitated, the uterus weight is determined, and the oxytocin receptor mRNA level is studied by means of in situ hybridization in suitable brain sections. The $ED_{50}$ values are determined with respect to stimulation of uterus growth and induction of the oxytocin receptor mRNA.

Production of the Compounds According to the Invention

For the production of the compounds according to the invention, i.e., modified/substituted derivatives of estra-1,3, 5(10)-triene-3,16ξ-diols, mainly two generally applicable synthesis strategies are used.

On the one hand, especially 3,16-protected derivatives of estra-1,3,5(10)-triene-3,16ξ-diols can be used, however, optionally also the free diols can be used for modifications to individual positions of the skeleton.

The synthesis of 11-nitrate esters represents a typical example. The known diacetate of estra-1,3,5(10)-triene-3, 16β-diol (J. Biol. Chem. 1955, 213, 343), which first is oxidized in C(9) and C(11)-positions according to a method by Sykes et al. (Tetrahedron Letters 1971, 3393), forms the starting point. The reductive removal of the benzylic C(9)-hydroxyl group already yields the 11-nitrate ester of estra-1,3,5(10)-triene-3,11β,16β-triol that is protected as a diacetate. After saponification, the epimeric 11-nitrate ester of estra-1,3,5(10)-triene-3,16α-diol then results from an inversion of the C(16)-hydroxyl group. The synthesis diagram that is outlined above can also run in reverse, if the diacetate of the estra-1,3,5(10)-triene-3,16α-diol is selected as a starting point. In this way, the 11-nitrate ester in the 16α-hydroxy series is produced first. Other compounds that result from intermediate products, such as, e.g., 11-nitrate esters of estra-1,3,5(10)-triene-3,9,11β-16ξ-tetraole are also obtained after cleavage of protective groups at C(3), C(16).

On the other hand, corresponding modified estrone analogs, which can be obtained in large numbers in known methods (characteristic but not limiting synthesis processes, which are useful for provision of representative substation patterns in the estrone skeleton, also in combination in several substituents, are found in, for example, C(1) J. Chem. Soc. (C) 1968, 2915; C(7) Steroids 54, 1989, 71; C(8α) Tetrahedron Letters 1991, 743; C(8β) Tetrahedron Letters 1964, 1763; Tetrahedron 1969, 25, 4011; J. Org. Chem. 1970, 35, 468; C(11) J. Steroid Biochem. 31, 1988, 549; C(9) J. Chem. Soc. Perk. 1 1973, 2095; C(15) J. Chem. Soc. Perk. 1 1996, 1269), offer flexible access to the compounds according to the invention by transposition of the oxygen functionality (Z. Chem. 1970, 221) of C(17) to C(16). Such novel derivatives of estrone are also suitable for this purpose, however.

For the case of C(3)-methyl ether of 8α-estra-1,3,5(10)-trien-17-one (Bull. Soc. Chim. Fr. 1967, 561), an in-depth typical description is given. After the ketone is converted into a sulfonylhydrazone, in the simplest case by reaction with phenylsulfonyl hydrazide, the formation of the C(16)—C(17) olefin is carried out in a decomposition reaction (Z. Chem. 1970, 10, 221–2; Liebigs Ann. Chem. 1981, 1973–81), on which hypobromide is stored in a regio/stereocontrolled way. Reductive dehalogenation and removal of the protective group at C(3) produce the 16β-alcohol, which can be converted into the 16α-epimer according to known methods.

Another variant for the introduction of the hydroxyl group to C atom 16 exists in the hydroboration of the 16(17)-double bond with sterically exacting boranes. It is known of this reaction that it results in 16-oxygenated products (Indian J. Chem. 1971, 9, 287–8). Consequently, the reaction of 3-methoxyestra-1,3,5(10),16-tetraene and 3-methoxy-18α-homoestra-1,3,5(10),16-tetraene with 9-borabicyclo[3.3.1] nonane produces 16α-hydroxyestratrienes after oxidation with alkaline hydrogen peroxide. To a lesser extent, the epimeric 16β-hydroxy steroids are formed in this reaction. After the cleavage of the 3-methoxy group, estra-1,3,5(10)-3,16α-diols are obtained. By inversion of the configuration at C atom 16, e.g., by Mitsunobu reaction (Synthesis 1980, 1), the 16β-hydroxyestratrienes are in turn obtained.

The broad applicability of the synthesis method that is outlined above is demonstrated in additional examples, thus, for example, for 3-methoxy-7α-methylestra-1,3,5(10)-trien-17-one (Helv. Chim. Acta 1967, 281) or 1,3-dimethoxy-1, 3,5(10)-trien-17-one (J. Org. Chem. 1967, 32, 4078).

The production of the central C(16)–C(17) olefinic intermediate stages is not limited to the arylsulfonylhydrazone method. If substituents on the steroid skeleton are not compatible with the basic reaction conditions of olefination, other processes, especially the conversion of the C(17) ketones into vinyl iodide (Tetrahedron 1988, 147) or enol triflates (Tetrahedron Letters 1984, 4821) and their subsequent reduction are suitable as alternatives.

If a synthesis pathway that runs through C(16)-keto derivatives, which then are converted into C(16)-alcohols or, by inversion, into C(16)a-alcohols, is selected, the possibilities for C(17)—→C(16)-ketotransposition are also selected. For a concrete example, refer to J. Chem. Soc. Perk. 1, 1976, 1350.

The introduction of fluorine atoms on carbon atoms 15 and 17 of the 16-hydroxyestratrienes according to the invention is possible by hydroboration of 15-fluoroestra-1,3,5 (10),16-tetraenes or 17-fluoroestra-1,3,5(10),16-tetraenes with a sterically exacting borane and oxidation with alkaline hydrogen peroxide. The synthesis of 15-fluoroestra-1,3,5 (10),16-tetraenes can be carried out from, for example, 15-hydroxyestra-1,3,5(10)-trien-17-ones. First, the secondary hydroxyl group must be substituted on carbon atom 15 by a fluorine atom. In this respect, for example, the 15α-hydroxyestrone that is accessible according to U.S. Pat. No. 3,375,174 is converted with known processes into 15β-fluoroestrone, by being reacted with diethylamino sulfur trifluoride or the corresponding 15α-mesylate being reacted with tetra-n-butylammonium fluoride (J. Chem. Res. (M) 1979, 4728–55). The thus accessible 15β-fluoroestra-1,3,5 (10)-trien-17-ones are converted into tosyl hydrazones. The Bamford-Stevens reaction of the 15-fluorinated tosyl hydrazones produces the 15-fluoroestra-1,3,5(10),16-tetraenes that are required for the introduction of the 16-hydroxyl group. The 17-fluoroestra-1,3,5(10),16-tetraenes that are necessary for the synthesis of 17-fluorinated 16-hydroxyestratrienes are accessible according to established processes. Corresponding ketones can be converted into geminal difluorides by reaction with sulfur tetrafluoride (J. Org. Chem. 1971, 36, 818–20) or dialkylaminosulfur trifluorides, such as diethylaminosulfur trifluoride (U.S. Pat. No. 3,976, 691). Hydrogen fluoride can be eliminated from these geminal difluorides by heating with aluminum oxide in an inert solvent according to U.S. Pat. No. 3,413,321, whereby fluoro-olefins are obtained. In addition, such fluoro-olefins can be obtained directly from ketones, if the ketones are reacted with diethylaminosulfur trifluoride in polar solvents with the addition of strong acids, e.g., fuming sulfuric acid (U.S. Pat. No. 4,212,815). The 17-fluoroestra-1,3,5(10),16-tetraen-3-ol that is described in U.S. Pat. No. 3,413,321 can be converted into a 17β-fluoroestra-1,3,5(10)-trien-3,16α-ol after the reaction with a sterically exacting borane and subsequent oxidation with alkaline hydrogen peroxide.

As a further modification, the introduction of double bonds may be useful. In addition to their pharmacological importance as selective estrogens in the context of this invention, these unsaturated derivatives represent valuable intermediate products for the synthesis of novel 16-hydroxyestra-1,3,5(10)-trienes. Below, the procedure for introducing a 9(11)-double bond is explained: A-ring-aromatic steroids are converted into the 9α-hydroxy steroids by dimethyl dioxiram; their dehydration results in estra-1,3,5(10),9(11)-tetraenes (Tetrahedron 1994, 50, 10709–20). By action of in-situ-produced dimethyl dioxiram on 18α-homoestra-1,3, 5(10)-triene-3,16α-diyldiacetate, the corresponding 9α-hydroxy compound can be produced. The dehydration of this tertiary alcohol results in 18α-homoestra-1,3,5(10),9(11)-tetraene-3,16α-diyldiacetate. After saponification, 18α-homoestra-1,3,5(10),9(11)-tetraene-3,16α-diol is obtained.

The compounds of general formula I according to the invention are produced as described in the examples. Additional compounds of general formula I can be obtained by an analogous procedure using reagents that are homologous to the reagents that are described in the examples.

Etherification and/or esterification of free hydroxy groups is carried out according to methods that are common to one skilled in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above, and of corresponding German application No. 199 06 159.9 filed Feb. 9, 1999, is hereby incorporated by reference.

EXAMPLE 1

8α-Estra-1,3,5(10)-triene-3,16β-diol

3-Methoxy-8α-estra-1,3,5(10)-trien-17-one-17-phenylsulfonylhydrazone

A suspension of 5.68 g (20 mmol) of 3-methoxy-8α-estra-1,3,5(10)-trien-17-one and 4.30 g (25 mmol) of benzenesulfonic acid hydrazide in 70 ml of ethanol is mixed with 3 drops of concentrated hydrochloric acid and then allowed to react at a bath temperature of 80–90° C. for three hours while being stirred vigorously. After the reaction solution is cooled, the precipitated product is suctioned off, rewashed with a little cold ethanol, and the hydrazone is dried in a vacuum. 8.10 g (92%) of product, which melts at 183–185° C., is obtained.

3-Methoxy-8α-estra-1,3,5(10),16-tetraene

A suspension of 8.10 g (18.5 mmol) of the above-described hydrazone in 140 ml of dry ether is cooled in an ice bath in a moisture-free environment (argon atmosphere) to 0° C. and mixed drop by drop with 36 ml of methyllithium (57 mmol) in ether. After the addition is completed, the cold bath is removed and stirred for another 3 hours at room temperature. For working-up, the reaction mixture is cooled to 0° C. and carefully mixed with saturated aqueous ammonium chloride solution (30 ml) while being stirred vigorously. This mixture is mixed with ethyl acetate, the organic phase is washed with water/brine and dried on sodium sulfate. The crude product is chromatographed on silica gel (hexane/ethyl acetate, 95:5). 3.60 g (72%) of product is obtained.

17α-Bromo-3-methoxy-8α-estra-1,3,5(10)-trien-16α-ol 3.40 g (12.67 mmol) of the olefin in 75 ml of dimethyl sulfoxide is brought into solution, then mixed with 5 ml of water, and 2.80 g of N-bromosuccinimide (15.75 mmol) in one portion is added while being stirred vigorously. For working-up after 4.5 hours of reaction at room temperature, the reaction solution is poured onto water, extracted with ethyl acetate (300 ml), the organic phase is washed first with water, then with brine and dried on sodium sulfate. The crude product is chromatographed on silica gel (toluene/acetone, 9:1), yield 3.50 g (75%) as an oil.

3-Methoxy-8α-estra-1,3,5(10)-trien-16β-ol

A solution of 3.50 g (9.60 mmol) of 17α-bromo-3-methoxy-8α-estra-1,3,5(10)-trien-16β-ol, 3.50 g (12.03 mmol) of tributyl tin hydride and 50 mg of azobisisobutyronitrile in 30 ml of dry tetrahydrofuran is refluxed for 2 hours while being stirred in an argon atmosphere. For working-up, it is allowed to cool, concentrated by evaporation in a vacuum in a Rotavapor, and the residue is taken up in ethyl acetate (300 ml). After the organic phase is washed with aqueous hydrochloric acid, water and brine, it is dried on sodium sulfate. The residue is chromatographed on silica gel (dichloromethane/ethyl acetate, 9:1), yield 2.70 g (98%).

8α-Estra-1,3,5(10)-triene-3,16β-diol (1)

A solution of 1.10 g (3.80 mmol) of methyl ether in 35 ml of diisobutyl aluminum/toluene (1.2 molar solution) is refluxed for 4 hours under an argon atmosphere in a moisture-free environment. Then, the reaction mixture is cooled in an ice bath and carefully mixed with ethyl acetate/water while being stirred. The precipitate that is produced is separated by filtration, thoroughly rewashed with ethyl acetate, and the organic phase is concentrated in a vacuum. The crude product is recrystallized from acetone/hexane, yield 679 mg (65%), melting point 181–182° C., rotation [α]D+13.60 (c 0.52, CH$_3$OH).

EXAMPLE 2

8α-Estra-1,3,5(10)-triene-3,16α-diol

3-Methoxy-8α-estra-1,3,5(10)-trien-16α-ol 1.22 ml (7.85 mmol) of azodicarboxylic acid diethyl ester, dissolved in 2 ml of toluene, is slowly added in drops to a mixture of 1.50 g (5.24 mmol) of 3-methoxy-8α-estra-1,3,5(10)-trien-16β-ol, 2.06 g (7.85 mmol) of triphenylphosphine and 0.3 ml of formic acid in 10 ml of toluene while being stirred. Then, it is allowed to react for two hours at room temperature. For working-up, it is taken up in ethyl acetate (300 ml), the organic phase is washed with water/brine and dried on sodium sulfate. The crude product is chromatographed on silica gel (hexane/acetone, gradient of up to 4:1). 1.40 g of 16α-formate is obtained, which is dissolved in 50 ml of 3% methanolic potassium hydroxide solution for saponification. After one hour at room temperature, it is mixed with aqueous hydrochloric acid, taken up in ethyl acetate (300 ml), the organic phase is washed with water/brine and dried on sodium sulfate. The crude product is chromatographed on silica gel (dichloromethane/ethyl acetate, gradient of up to 7:3), yield 940 mg (63%).

8α-Estra-1,3,5(10)-triene-3,16α-diol

A solution of 740 mg (2.58 mmol) of methyl ether in 25 ml of diisobutyl aluminum/toluene (1.2 molar solution) is refluxed for 4 hours in a moisture-free environment in an argon atmosphere (1300 bath temperature). Then, the reaction mixture is cooled in an ice bath and carefully mixed with ethyl acetate/water. The precipitate is separated by filtration, thoroughly rewashed with ethyl acetate, and the organic phase is concentrated in a vacuum. The crude product is recrystallized from acetone/hexane, yield 323 mg (46%), melting point 239–240° C., rotation [α]$_D$+19.8° (c 0.52, CH$_3$OH).

EXAMPLE 3

7α-Methylestra-1,3,5(10)-triene-3,16β-diol

3-Methoxy-7α-methylestra-1,3,5(10)-trien-17-one-17-phenylsulfonylhydrazone 4.70 g (66%) of the corresponding phenylsulfonylhydrazone, which crystallizes out during cooling of the reaction mixture, is produced from 4.70 g (15.75 mmol) of 3-methoxy-7α-methylestra-1,3,5(10)-trien-17-one, melting point 167–170° C.

3-Methoxy-7α-methylestra-1,3,5(10),16-tetraene 2.35 g (85%) of olefin, which crystallized from ethanol as white scales after chromatography on silica gel (hexane/ethyl acetate, 9:1), resulted from the olefination of 4.40 g (9.72 mmol) of phenylsulfonylhydrazone, melting point 114–116° C.

17α-Bromo-3-methoxy-7α-methylestra-1,3,5(10)-trien-16β-ol

The bromohydrin formation with 2.00 g (7.08 mmol) of olefin produced 2.14 g (80%) of adduct, melting point 145–146° C. (ether/pentane), while being decomposed.

3-Methoxy-7α-methylestra-1,3,5(10)-trien-16β-ol 1.40 g (91%) of product, amorphous, was obtained from 1.94 g (5.12 mmol) of bromide by reductive dehalogenation.

7α-Methylestra-1,3,5(10)-triene-3,16β-diol (3)

The cleavage of 1.40 g (4.66 mmol) of methyl ether provided 1.25 g (92%) of the diol, whose melting point was 209–210° C. (acetone/hexane), [α]$_D$+73.8° (c 0.50, CH$_3$OH).

EXAMPLE 4

7α-Methylestra-1,3,5(10)-triene-3,16α-diol (4)

It was possible to obtain 0.434 g (59%) of the 16α-derivative from 0.74 g (2.58 mmol) of 3,16β-diol by epimerization/saponification at C(16), melting point 217–219° C. (acetone/hexane), [α]$_D$+84.4° (c 0.52, CH$_3$OH).

EXAMPLE 5

1-Methoxyestra-1,3,5(10)-triene-3,16β-diol 1,3-Dimethoxyestra-1,3,5(10)-trien-17-one-17-phenylsulfonylhydrazone According to the general recipe for hydrazone formation, 3.14 g (10 mmol) of 1,3-dimethoxyestra-1,3,5(10)-trien-17-one yielded 4.0 g (85%) of the 17-benzenesulfonic acid hydrazone, which recrystallized from the ethanolic reaction solution, melting point 200–202° C.

1,3-Dimethoxyestra-1,3,5(10),16-tetraene

The olefination of 4.0 g (8.54 mmol) of hydrazone resulted in 1.96 g (76%) of tetraene, which was recrystallized from ethanol after chromatography, melting point 109–111° C.

1,3-Dimethoxyestra-1,3,5(10)-trien-16β-ol 0.872 g (55%) of the 16β-alcohol was obtained from 1.50 g (5.03 mmol) of the olefin by bromohydrin formation and dehalogenation.

1,3-Dimethoxyestra-1,3,5(10)-trien-16α-ol

The inversion of 0.50 g (1.58 mmol) of 16β-alcohol yielded 0.46 g (92%) of the 16α-epimer.

1-Methoxyestra-1,3,5(10)-triene-3.16β-diol (5)

0.25 g (0.79 mmol) of 1,3-dimethoxy derivative was monodemethylated to 0.18 g (75%) of methoxydiol. Melting point after trituration in toluene 90–93° C.

EXAMPLE 6

1-Methoxyestra-1,3,5(10)-triene-3,16α-diol (6)

The demethylation of 0.35 g (1.11 mmol) of dimethoxy derivative in the 16α-series produced 0.218 g (65%) of monomethylether, melting point 240–242° C. (acetone/chloroform).

EXAMPLE 7

3,11β,16β-Trihydroxyestra-1,3,5(10)-triene-11-nitrate ester 3,16β-Diacetyloxyestra-1,3,5(10)-triene 8.00 g (29.4 mmol) of estra-1,3,5(10)-triene-3,16β-diol is introduced at room temperature into 50 ml of pyridine, it is mixed with 10 ml of acetic acid anhydride while being stirred and then allowed to react overnight. For working-up, the reaction mixture is put into ice water (3 l), whereby the reaction product is deposited as precipitate. The precipitate is collected on a frit, washed thoroughly with distilled water, dried, and finally taken up in dichloromethane (500 ml). The organic phase is washed with dilute bicarbonate solution and water and dried on sodium sulfate. The organic residue is recrystallized from acetone/hexane, yield 8.40 g (80%).

3,16β-Diacetyloxy-9,11β-dihydroxyestra-1,3,5(10)-triene-11-nitrate ester

A suspension of 7.85 g (22.0 mmol) of 3,16β-diacetyloxyestra-1,3,5(10)-triene in 200 ml of aqueous acetic acid (90%) is mixed for ten minutes in portions with 60.31 g (110 mmol) of cerium ammonium nitrate while being stirred. The steroidal educt goes into solution during the course of the reaction. After five hours, the reaction solution is poured onto ice water (6 l), and the yellow-red-colored precipitate is suctioned off, which is then dried in air. The crude product is then taken up in ethyl acetate (600 ml), the organic phase is washed with water/brine and dried on sodium sulfate. The red-brown-colored crude product is chromatographed on silica gel (dichloromethane/ethyl acetate, 9:1), yield 5.10 g (53%), melting point 173–175° C. (acetone/hexane).

3,16β-Diacetyloxyestra-1,3,5(10)-trien-11β-ol-11-nitrate ester 5.0 ml of boron trifluoride-etherate is added in drops to a solution of 2.42 g (5.58 mmol) of 3,16β-diacetyloxyestra-1,3,5(10)-triene-9,11β-diol-11-nitrate ester and 2.90 ml (18.31 mmol) of triethylsilane in 60 ml of dry dichloromethane that is cooled to −15° C. while being stirred. It is allowed to react first for one hour at −15° C., then for another hour at 0° C. before the reaction mixture is stirred into bicarbonate-containing ice water. The product mixture is extracted with dichloromethane, the organic phase is washed with water and dried on sodium sulfate. The crude product is chromatographed on silica gel (hexane/ethyl acetate, gradient of up to 7:3). Yield 1.58 g (68%), melting point 188–190° C. (acetone/hexane).

3,11β,16β-Trihydroxyestra-1,3,5(10)-triene-11-nitrate ester (7)

1.31 g (3.14 mmol) of the above-described diacetate is taken up in 60 ml of dichloromethane, mixed with 20 ml of methanolic potassium hydroxide solution (3%) and stirred for four hours in a protective gas atmosphere (argon). For working-up, it is mixed with 500 µl of acetic acid, diluted with dichloromethane, the organic phase is washed with water and dried on sodium sulfate. The crude product is recrystallized from dichloromethane, yield 874 mg (83%), melting point 170–171° C., while being decomposed. $[\alpha]_D$+68.9° (c 0.52, $CH_3OH$).

EXAMPLE 8

3,11β,16α-Trihydroxyestra-1,3,5(10)-triene-11-nitrate ester (8)

2.26 g (8.62 mmol) of triphenylphosphine and 325 µl of formic acid are added to a solution of 820 mg (2.46 mmol) of 3,16β-diol in 25 ml of dry tetrahydrofuran. Then, 1.34 ml (8.62 mmol) of azodicarboxylic acid diethyl ester is slowly added in drops at room temperature to this solution while being stirred. After addition has been completed, it is stirred for another 30 minutes at room temperature before the reaction solution is poured onto water and extracted with ethyl acetate. The organic phase is washed with water/brine and dried on sodium sulfate. The crude product is taken up in 20 ml of dichloromethane, mixed with 10 ml of methanolic potassium hydroxide solution (3%) and stirred for 2.5 hours at room temperature in an environment devoid of atmospheric oxygen. For working-up, it is acidified with dilute hydrochloric acid, extracted with dichloromethane (200 ml), washed with water and dried on sodium sulfate. The crude product is chromatographed on silica gel (dichloromethane/acetone, gradient of up to 4:1), yield 704 mg (85%) as a foam.

$[\alpha]_D$+71.4° (c 0.50, $CH_3OH$).

EXAMPLE 9

18α-Homoestra-1,3,5(10)-triene-3,16α-diol

3-Methoxy-18α-homoestra-1,3,5(10)-triene-3,16α-diol 7.41 g of 3-methoxy-18α-homoestra-1,3,5(10),16-tetraene is dissolved in 50 ml of anhydrous tetrahydrofuran under protective gas and mixed with 6.4 g of 9-borabicyclo [3.3.1]nonane. It is stirred at room temperature until reaction has been completed. Then, it is mixed with 75 ml of water. After gas generation has been completed, 45 ml of 3 M sodium hydroxide solution is added. 45 ml of hydrogen peroxide solution (30%) is then slowly added in drops to the reaction mixture while being cooled. It is stirred for 1 hour at room temperature and extracted with ethyl acetate. The chromatography of the crude product on silica gel (eluant: cyclohexane/ethyl acetate 3+1) yields 6.03 g of 18α-homoestra-1,3,5(10)-triene-3,16α-diol. After recrystallization from methanol, colorless crystals are obtained; flash point 109 . . . 111° C.; $[\alpha]_D=+71°$ (chloroform, c=1.02).

18α-Homoestra-1,3,5(10)-triene-3,16α-diol (9)

2 g of 3-methoxy-18α-homoestra-1,3,5(10)-trien-16α-ol is suspended under protective gas in 40 ml of toluene. 26 ml of a solution of diisobutyl aluminum hydride (30% by vol.) in toluene is added in drops to this suspension and refluxed until the reaction has been completed (about 10 hours). 10.6 ml of ethanol and, carefully while being cooled, 32 ml of semiconcentrated hydrochloric acid are added to the cooled batch. After extraction with ethyl acetate, 1.85 g of crude 18α-homoestra-1,3,5(10)-triene-3,16α-diol is obtained. Recrystallization from ethyl acetate yields 1.34 g of colorless crystals; flash point 194 . . . 198° C.; $[\alpha]_D=+69°$ (dioxane, c=0.99).

EXAMPLE 10

18α-Homoestra-1,3,5(10)-triene-3,16β-diol (10)

0.5 g of 18α-homoestra-1,3,5(10)-triene-3,16α-diol is dissolved in 25 ml of toluene with the addition of 3.66 g of triphenylphosphine and 3.42 g of 4-nitrobenzoic acid. 6.4 ml of diethylazodicarboxylate solution (40% in toluene) is slowly added in drops to the above. After 48 hours of reaction at room temperature, it is diluted with ethyl acetate, and the organic phase is washed with sodium bicarbonate solution, water and sodium chloride solution. It is dried on magnesium sulfate and concentrated by evaporation.

The product that is obtained is dissolved in 30 ml of methanol and mixed with 4.82 g of potassium carbonate. It is stirred at room temperature until saponification has been completed. For working-up, the main amount of methanol is distilled off, and the residue is taken up in ethyl acetate. It is washed with sodium chloride solution and dried on magnesium sulfate. After concentration by evaporation, 0.45 g of crude 18α-homoestra-1,3,5(10)-triene-3,16β-diol is obtained. The recrystallization from ethyl acetate yields 0.26 g of colorless crystals; flash point 210 . . . 213° C.; $[\alpha]_D=+67°$ (dioxane, c=1.01).

EXAMPLE 11

18α-Homoestra-1,3,5(10),9(11)-tetraene-3,16α-diol

18α-Homoestra-1,3,5(10)-triene-3,16α-diyldiacetate 1 g of 18α-homoestra-1,3,5(10)-triene-3,16α-diol is mixed with 4 ml of pyridine and 4 ml of acetic anhydride and 10 mg of 4-dimethylaminopyridine and allowed to stand overnight. For working-up, it is mixed with ice and extracted with ethyl acetate. The combined extracts are washed with copper sulfate solution (10%) and saturated sodium chloride solution and dried on magnesium sulfate. 1.32 g of 18α-homoestra-1,3,5(10)-triene-3,16α-diyldiacetate is isolated methylene chloride, 18 ml of water, 15 ml of acetone, 5.4 g of sodium bicarbonate and 12 mg of tetra-n-butylammonium hydrogen sulfate. After temperature equalization to 10° C., 11.1 g of potassium monopersulfate (Caroat®) is successively added. The reaction mixture was stirred for 4.5 hours at 10° C. Then, it was filtered with a frit to separate the salts, and the organic phase of the filtrate was separated. The aqueous phase is subsequently re-extracted with methylene chloride, and the combined extracts are dried on magnesium sulfate. After the solvent is evaporated, 1.73 g of crude 9α-hydroxy-18α-homoestra-1,3,5(10)-triene-3,16α-diyldiacetate is obtained. The latter is dissolved in 12 ml of methylene chloride. The solution is temperature-equalized to −10° C. and mixed with 0.16 ml of sulfuric acid (70%). After the reaction has been completed, it is mixed with saturated sodium bicarbonate, and the organic phase is separated. After the solvent is dried and evaporated, 1.33 g of a brown oil is obtained. The purification on silica gel (eluant: cyclohexane/ethyl acetate 3+1) yields 0.63 g of 18α-homoestra-1,3,5(10),9(11)-tetraene-3,16α-diyldiacetate as a colorless foam.

18α-Homoestra-1,3,5(10),9(11)-tetraene-3,16α-diol (11)

0.63 g of 18α-homoestra-1,3,5(10),9(11)-tetraene-3,16α-diyldiacetate is dissolved in 50 ml of methanol and mixed with 4.72 g of potassium carbonate. It is stirred at room temperature until saponification has been completed. For working-up, the main amount of methanol is distilled off, and the residue is taken up in ethyl acetate. It is washed with sodium chloride solution and dried on magnesium sulfate. After concentration by evaporation, 0.49 g of 18α-homoestra-1,3,5(10),9(11)tetraene-3,16α-diol is obtained as a yellowish crystallizate.

EXAMPLE 12

Estra-1,3,5(10),9(11)-tetraene-3,16α-diol

Estra-1,3,5(10),9(11)-tetraene-3,16α-diyldiacetate

Analogously to Example 11, 12.69 g (35.8 mmol; 64% of theory) of estra-1,3,5(10),9(11)-tetraene-3,16α-diyldiacetate is obtained starting from 19.9 g (55.82 mmol) of estra-1,3,5(10)-triene-3,16α-diyldiacetate.

Estra-1,3,5(10),9(11)-tetraene-3,16α-diol

Analogously to Example 11, 12.5 g (35.26 mmol) of estra-1,3,5(10),9(11)-tetraene-3,16α-diyldiacetate is saponified. 9.53 g (35.26 mmol; 99% of theory) of estra-1,3,5(10), 9(11)-tetraene-3,16α-diol is obtained as almost colorless crystallizate. Recrystallization from ethyl acetate yields colorless crystals; flash point 237 . . . 244° C.; $[\alpha]_D$=###° (., c=###).

EXAMPLE 13

13α-Estra-1,3,5(10)-triene-3,16α-diol

3-Methoxy-17-tosylhydrazono-13α-estra-1,3,5(10)-triene 2.5 g (8.79 mmol) of 3-methoxy-13α-estra-1,3,5(10)-trien-17-one and 1.96 g (10.55 mmol) of tosylhydrazide are refluxed in 15 ml of a mixture that consists of ethanol and glacial acetic acid (4+1, v/v) for 6 hours. The cooled reaction solution is mixed with saturated sodium bicarbonate solution and extracted with ethyl acetate. The organic phase is washed with saturated sodium bicarbonate solution and with saturated sodium chloride solution and dried on magnesium sulfate. The dark brown oil that is obtained is chromatographed on silica gel (eluant: cyclohexane/ethyl acetate 4+1). 2.49 g of a colorless, amorphous solid is obtained; $[\alpha]_D$=−58° (dioxane, c=0.99).

3-Methoxy-13α-estra-1,3,5(10),16-tetraene 2.43 g (5.37 mmol) of 3-methoxy-17-tosylhydrazono-13α-estra-1,3,5(10)-triene is suspended in 20 ml of anhydrous methyl-tert-butylether. 1.61 ml of a 10 M n-butyl-lithium solution in hexane is slowly added in drops to this suspension. It is stirred for 1 hour at room temperature. While being cooled, 50 ml of saturated ammonium chloride solution is added in drops. After the organic phase is separated, it is extracted with ethyl acetate. The combined organic phases are washed with water and saturated sodium chloride solution and dried (MgSO$_4$). The crude product (2.1 g of brown oil) is chromatographed on silica gel, whereby 0.81 g of 3-methoxy-13α-estra-1,3,5(10),16-tetraene is obtained as a colorless oil; $[\alpha]_D$=−6° (chloroform; c=0.94).

3-Methoxy-13α-estra-1,3,5(10)-trien-16α-ol 0.81 g (3 mmol) of 3-methoxy-13α-estra-1,3,5(10),16-tetraene is dissolved under a cover gas in 10 ml of anhydrous tetrahydrofuran and mixed with 0.73 g of 9-bora-bicyclo[3.3.1]nonane. It is stirred at room temperature until the reaction is completed. Then, it is mixed with 15 ml of water. After gas generation is completed, 7.8 ml of 3 M sodium hydroxide solution is added. 7.8 ml of hydrogen peroxide solution (30%) is then slowly added in drops to the reaction mixture while being cooled. It is stirred for 1 hour at room temperature and extracted with ethyl acetate. The chromatography of the crude product on silica gel (eluant: cyclohexane/ethyl acetate 4+1) yields 604 mg of 3-methoxy-13α-estra-1,3,5(10)-trien-16α-ol in the form of a colorless oil.

13α-Estra-1,3,5(10)-triene-3,16α-diol 0.55 g of 3-methoxy-13α-estra-1,3,5(10)-trien-16α-ol is dissolved hot under a cover gas in 10 ml of toluene. A mixture of 2.3 ml of diisobutylaluminum hydride and 5.4 ml of toluene is added in drops to this solution and refluxed until the reaction is completed (about 4 hours). 2.1 ml of ethanol is added to the cooled batch, and 6 ml of semi-concentrated hydrochloric acid is carefully added while being cooled. After extraction with ethyl acetate, the organic phase is washed neutral and dried on magnesium sulfate. 362 mg of 13α-estra-1,3,5(10)-triene-3,16α-diol is obtained. The recrystallization from methanol yields colorless crystals; flash point 224 . . . 231° C.; $[\alpha]_D$=+61° (pyridine, c=1.13).

EXAMPLE 14

9β-Estra-1,3,5(10)-triene-3,16α-diol

3-Methoxy-17-tosylhydrazono-9β-estra-1,3,5(10)-triene

Produced analogously to Example 13. Colorless foam.

3-Methoxy-9β-estra-1,3,5(10),16-tetraene

Produced analogously to Example 13. Colorless oil.

3-Methoxy-9β-estra-1,3,5(10)-trien-16α-ol

Produced analogously to Example 13. Colorless oil.

9β-Estra-1,3,5(10)-triene-3,16α-diol

Produced analogously to Example 13. Colorless crystals; flash point 140 . . . 145° C.; $[\alpha]_D$=###° (c=).

EXAMPLE 15

3,16α-Bis(benzyloxy)-18α-homoestra-1,3,5(10)-trien-1'-one 3,16α-Bis(benzyloxy)-18α-homoestra-1,3,5(10),9(11)-tetraene 4 g of sodium hydride (80% in paraffin oil, 25.52 mmol) is added under a cover gas to 32 ml of anhydrous N,N-dimethylformamide. A solution of 7.67 (26.97 mmol) of 18α-homoestra-1,3,5(10)-triene-3,16α-diol in 40 ml of tetrahydrofuran is added in drops to this mixture. After gas generation is completed, 13.84 g (80.91 mmol) of benzyl bromide is added. After the reaction is completed, the reaction solution is slowly added in drops to water (about 1 l). After extraction with ethyl acetate, 14 g of brown oil is obtained. Chromatography on silica gel yields 10.2 g (21.9 mmol; 81.3% of theory) of 3,16α-bis(benzyloxy)-18α-homoestra-1,3,5(10),9(11)-tetraene as a colorless oil; $[\alpha]_D$=+110° (chloroform, c=1.01).

3,16α-Bis(benzyloxy)-18α-homoestra-1,3,5(10)-trien-11α-ol 10 g (21.5 mmol) of 3,16α-bis(benzyloxy)-18α-homoestra-1,3,5(10),9(11)-tetraene is dissolved under a cover gas in 60 ml of anhydrous tetrahydrofuran, and 12.9 g (107.61 mmol) of catechol borane and 0.99 g (43.1 mmol) of lithium borohydride are added. After the reaction is completed, it is carefully hydrolyzed with 100 ml of water. 95 ml of 3N sodium hydroxide solution is then added, and 95 ml of hydrogen peroxide (30%) is added in drops while being cooled. It is stirred for 1 hour at room temperature and subsequently extracted with ethyl acetate. The chromatography of the crude product on silica gel (eluant: cyclohex ane/ethyl acetate 4+1) yields 8.73 g (18.08 mmol; 84% of theory) of 3,16α-bis(benzyloxy)-18α-homoestra-1,3,5(10)-trien-11α-ol as a colorless foam; $[α]_D$=###° (., c=###).

3,16α-Bis(benzyloxy)-18α-homoestra-1,3,5(10)-trien-11-one 0.89 g (1.84 mmol) of 3,16α-bis(benzyloxy)-18α-homoestra-1,3,5(10)-trien-11α-ol is dissolved in 20 ml of methylene chloride and mixed with 0.98 g (4.6 mmol) of pyridium chlorochromate. It is stirred for 4 hours. The reaction mixture is then diluted with tetrachloromethane and filtered on silica gel. The filtrate is concentrated by evaporation and chromatographed on silica gel (eluant: cyclohexane/ethyl acetate 4+1). 0.63 g (1.31 mmol; 71% of theory) of 3,16α-bis(benzyloxy)-18α-homoestra-1,3,5(10)-trien-11-one is obtained as a colorless solid; $[α]_D$=###° (., c=###).

EXAMPLE 16

3,16α-Bis(benzyloxy)estra-1,3,5(10)-trien-11-one 3,16α-Bis(benzyloxy)estra-1,3,5(10),9(11)-tetraene Analogously to Example 15, 12.83 g (28.47 mmol; 88% of theory) of 3,16α-bis(benzyloxy)estra-1,3,5(10),9(11)-tetraene is obtained as a colorless oil from 8.7 g (32.17 mmol) of estra-1,3,5(10),9(11)-tetraene-3,16α-diol; $[α]_D$=+96° (chloroform, c=1).

3,16α-Bis(benzyloxy)estra-1,3,5(10)-trien-11α-ol

Analogously to Example 15, 9.43 g (20.2 mmol; 71% of theory) of 3,16α-bis(benzyloxy)-estra-1,3,5(10)-trien-11α-ol is obtained as a colorless solid from 12.74 g (28.27 mmol) of 3,16α-bis(benzyloxy)-estra-1,3,5(10),9(11)-tetraene; $[α]_D$=###° (., c=###).

3,16α-Bis(benzyloxy)estra-1,3,5(10)-trien-11-one

Analogously to Example 15, 1.91 g (4.09 mmol; 64% of theory) of 3,16α-bis(benzyloxy)estra-1,3,5(10)-trien-11-one is obtained from 3 g (6.4 mmol) of 3,16α-bis(benzyloxy) estra-1,3,5(10)-trien-11α-ol; $[α]_D$=###° (., c=###).

EXAMPLE 17

9α-Methyl-18α-homoestra-1,3,5(10)-triene-3,16α-diol 3,16α-Bis(benzyloxy)-9α-methyl-18α-homoestra-1,3,5(10)-trien-11-one Under a cover gas, 0.8 g (7.13 mmol) of potassium-tert-butylate is dissolved in 6.26 ml of tert-butanol; 0.8 g (1.66 mmol) of 3,16α-bis(benzyloxy)-18α-homoestra-1,3,5(10)-trien-11-one is dissolved in 15.57 ml of methyl iodide and added in drops to the first solution. After 15 minutes, 50 ml of saturated sodium chloride solution is added. The extraction with ethyl acetate yields a yellow foam, which is chromatographed on silica gel (eluant: cyclohexane/ethyl acetate 7+1). 0.6 g (1.21 mmol; 73% of theory) of 3,16α-bis(benzyloxy)-9α-methyl-18α-homoestra-1,3,5(10)-trien-11-one is obtained as a colorless foam; $[α]_D$=+216° (chloroform, c=1.03).

3,16α-Bis(benzyloxy)-9α-methyl-18α-homoestra-1,3,5(10)-triene 0.76 g (1.54 mmol) of 3,16α-bis(benzyloxy)-9α-methyl-18α-homoestra-1,3,5(10)-trien-1'-one is introduced into a flask with 5 ml of triethylene glycol. A solution of 2.16 g (38.15 mmol) of potassium hydroxide in 15 ml of triethylene glycol and 1.54 g (30.8 mmol) of hydrazine hydrate are added to this mixture. This mixture is heated for 4 hours to 210° C. Then, it is mixed with saturated sodium chloride solution and extracted with ethyl acetate. The organic phases are washed with dilute hydrochloric acid, water and sodium chloride solution. The crude product is chromatographed on silica gel (eluant: cyclohexane/ethyl acetate 14+1). In this case, 0.66 g (1.37 mmol; 89% of theory) of 3,16α-bis(benzyloxy)-9α-methyl-18α-homoestra-1,3,5(10)-triene accumulates as a colorless oil; $[α]_D$=+47° (chloroform, c=0.93).

9α-Methyl-18α-homoestra-1,3,5(10)-triene-3,16α-diol 0.65 g (1.37 mmol) of 3,16α-bis(benzyloxy)-9α-methyl-18α-homoestra-1,3,5(10)-triene is dissolved in 20 ml of tetrahydrofuran, mixed with 0.65 g of palladium-carbon (10% Pd) and hydrogenated. The catalyst is filtered off, and the filtrate is concentrated by evaporation, whereby 0.4 g (1.33 mmol; 97% of theory) of 9α-methyl-18α-homoestra-1,3,5(10)-triene-3,16α-diol remains. Recrystallization from methanol yields colorless crystals; flash point 210 . . . 215° C.; $[α]_D$=###° (., c=###).

EXAMPLE 18

9α-Methylestra-1,3,5(10)-triene-3,16α-diol 3,16α-Bis(benzyloxy)-9α-methylestra-1,3,5(10)-trien-11-one Analogously to Example 17, 0.379 g (0.78 mmol; 73% of theory) of 3,16α-bis(benzyloxy)-9α-methylestra-1,3,5(10)-trien-11-one is obtained as a colorless foam from 0.497 g (1.06 mmol) of 3,16α-bis(benzyloxy)estra-1,3,5(10)-trien-11-one; $[α]_D$=+231° (chloroform, c=1.03).

3,16α-Bis(benzyloxy)-9α-methylestra-1,3,5(10)-triene

Analogously to Example 17, 0.458 g (0.98 mmol; 66% of theory) of 3,16α-bis-(benzyloxy)-9α-methylestra-1,3,5(10)-triene is obtained as a colorless oil from 0.715 g (1.48 mmol) of 3,16α-bis(benzyloxy)-9α-methylestra-1,3,5(10)-trien-11-one; $[α]_D$=+61° (chloroform, c=1.16).

9α-Methylestra-1,3,5(10)-triene-3,16α-diol

Analogously to Example 17, 0.292 g (1 mmol; 99% of theory) of 9α-methylestra-1,3,5(10)-triene-3,16α-diol is obtained from 0.476 g (1.01 mmol) of 3,16α-bis(benzyloxy)-9αmethylestra-1,3,5 (10)-triene. The recrystallization yields colorless crystals; flash point 182 . . . 186° C.; $[α]_D$=###° (., c=###).

EXAMPLE 19

11β-Methyl-18α-homoestra-1,3,5(10)-triene-3,16α-diol 3,16α-Bis(benzyloxy)-11α-methyl-18α-homoestra-1,3,5(10)-trien-11β-ol 0.6 g (1.25 mmol) of 3,16α-bis(benzyloxy)-18α-homoestra-1,3,5(10)-trien-11-one is dissolved under a cover gas in 20 ml of anhydrous tetrahydrofuran. This solution is cooled to −15° C. and mixed with 4.17 ml of 3M methylmagnesium bromide solution. After the reaction is completed, saturated ammonium chloride solution is added and extracted with ethyl acetate. The crude product is chromatographed on silica gel (eluant: cyclohexane/ethyl acetate 6+1), whereby 0.59 g (1.18 mmol; 95% of theory) of 3,16α-bis(benzyloxy)-11α-methyl-18α-homoestra-1,3,5(10)-trien-11β-ol accumulates as a colorless oil; $[\alpha]_D$=−1° (chloroform, c=0.99).

3,16α-Bis(benzyloxy)-11β-methyl-18α-homoestra-1,3,5(10)-triene 0.5 g (1 mmol) of 3,16α-bis(benzyloxy)-11α-methyl-18α-homoestra-1,3,5(10)-trien-11β-ol is dissolved under a cover gas in methylene chloride and mixed with 1.75 g (2.4 ml; 15.3 mmol) of triethylsilane. It is cooled to −10° C. and mixed with 5.69 g (5 ml, 40 mmol) of boron trifluoride ethyl etherate. After the reaction is completed, it is mixed with saturated sodium bicarbonate solution and extracted. The crude product is purified on silica gel (eluant: cyclohexane/ethyl acetate 9+1). 0.327 g (0.68 mmol; 68% of theory) of 3,16α-bis(benzyloxy)-11β-methyl-18α-homoestra-1,3,5(10)-triene is isolated as a colorless oil; $[\alpha]_D$=+119° (chloroform, c=0.99).

11β-Methyl-18α-homoestra-1,3,5(10)-triene-3,16α-diol 0.45 g (0.93 mmol) of 3,16α-bis(benzyloxy)-11β-methyl-18α-homoestra-1,3,5(10)-triene is dissolved in 20 ml of tetrahydrofuran, mixed with 0.45 g of palladium-carbon (10% Pd) and hydrogenated. The catalyst is filtered off, and the filtrate is concentrated by evaporation, whereby 0.264 g (0.87 mmol; 94% of theory) of 11β-methyl-18α-homoestra-1,3,5(10)-triene-3,16α-diol remains. Recrystallization from ethyl acetate yields colorless crystals; flash point 244 . . . 251° C.; $[\alpha]_D$=###° (., c=###).

EXAMPLE 20

11β-Methyl-18α-homoestra-1,3,5(10)-triene-3,16β-diol 0.1 g (0.33 mmol) of 11β-methyl-18α-homoestra-1,3,5(10)-triene-3,16α-diol is dissolved in toluene with the addition of 0.35 g (1.33 mmol) of triphenylphosphine and 0.22 g (1.33 mmol) of 4-nitrobenzoic acid. 0.6 ml (1.33 mmol) of diethylazodicarboxylate solution (40% in toluene) is slowly added in drops to it. It is heated to 50° C. until the reaction is completed. Then, it is diluted with ethyl acetate, and the organic phase is washed with sodium bicarbonate solution, water and sodium chloride solution. It is dried on magnesium sulfate and concentrated by evaporation.

The product that is obtained is dissolved in 20 ml of methanol and mixed with 0.81 g (5.85 mmol) of potassium carbonate. It is stirred at room temperature until the saponification is completed. For working-up, the main amount of the methanol is distilled off, and the residue is taken up in ethyl acetate. It is washed with sodium chloride solution and dried on magnesium sulfate. The crude product is chromatographed on silica gel (eluant: cyclohexane/ethyl acetate 2+1), whereby 0.79 g (0.26 mmol; 78% of theory) of 11β-methyl-18α-homoestra-1,3,5(10)-triene-3,16β-diol is obtained. The recrystallization from ethyl acetate yields colorless crystals; flash point 175 . . . 188° C.; $[\alpha]_D$=???° (???, c=###).

EXAMPLE 21

11β-Methylestra-1,3,5(10)-triene-3,16α-diol 3,16α-Bis(benzyloxy)-11α-methylestra-1,3,5(10)-trien-11β-ol Produced analogously to Example 19. Colorless oil; $[\alpha]_D$=+2° (chloroform, c=0.92).

3,16α-Bis(benzyloxy)-11β-methylestra-1,3,5(10)-triene

Produced analogously to Example 19. Colorless oil; $[\alpha]_D$=+112° (chloroform, c=1).

11β-Methylestra-1,3,5(10)-triene-3,16α-diol

Produced analogously to Example 19. Colorless crystals from methyl-tert-butyl ether; flash point 243 . . . 250° C.; $[\alpha]_D$=+172° (dioxane, c=0.96).

EXAMPLE 22

11β-Methylestra-1,3,5(10)-triene-3,16β-diol

Produced analogously to Example 20. Colorless crystals from cyclohexane/ethyl acetate; flash point 194 . . . 199° C.; $[\alpha]_D$=###° (., c=###).

EXAMPLE 23

11β-Ethyl-18α-homoestra-1,3,5(10)-triene-3,16α-diol 3,16α-Bis(benzyloxy)-11α-ethyl-18α-homoestra-1,3,5(10)-trien-11β-ol Produced analogously to Example 19. Colorless oil.

3,16α-Bis(benzyloxy)-11β-ethyl-18α-homo estra-1,3,5(10)-triene

Produced analogously to Example 19. Colorless oil.

11β-Ethyl-18α-homoestra-1,3,5(10)-triene-3,16α-diol

Produced analogously to Example 19. Colorless crystals 242 . . . 255° C.

EXAMPLE 24

11β-Ethyl-18α-homoestra-1,3,5(10)-triene-3,16β-diol

Produced analogously to Example 20. Colorless crystals 152 . . . 156° C.

EXAMPLE 25

11β-Ethylestra-1,3,5(10)-triene-3,16α-diol 3,16α-Bis(benzyloxy)-11α-ethylestra-1,3,5(10)-trien-11β-ol Produced analogously to Example 19. Colorless oil; $[\alpha]_D=-3°$. (chloroform, c=1).

3,16α-Bis(benzyloxy)-11β-ethylestra-1,3,5(10)-triene

Produced analogously to Example 19. Colorless oil; $[\alpha]_D=+97°$ (chloroform, c=1).

11β-Ethylestra-1,3,5(10)-triene-3,16α-diol

Produced analogously to Example 19. Colorless crystals from ethyl acetate; flash point 245 . . . 250° C.; $[\alpha]_D=###°$ (., c=###).

EXAMPLE 26

11β-Ethylestra-1,3,5(10)-triene-3,16β-diol

Produced analogously to Example 20. Amorphous solid.

EXAMPLE 27

11β-Methoxy-estra-1,3,5(10)-triene-3,16α-diol

11β-Methoxy-17-tosylhydrazono-estra-1,3,5(10)-trien-3-ol

In a mixture of 6 ml of ethanol and 4 ml of glacial acetic acid, 1 g (3.3 mmol) of 3-hydroxy-11β-methoxy-estra-1,3,5(10)-trien-17-one and 0.7 g (3.8 mmol) of toluene-4-sulfonic acid hydrazide are refluxed. After a reaction time of about 5 hours at boiling heat, the reaction mixture is cooled, and the product is isolated in about 100 ml of water by addition in drops. By boiling the crude product in n-hexane, the water that is contained is azeotropically removed.

1.14 g of product (73% of theory) is obtained.

11β-Methoxy-estra-1,3,5(10),16-tetraen-3-ol 469 mg (1 mmol) of 11]-methoxy-17-tosylhydrazono-estra-1,3,5(10)-trien-3-ol is introduced into 15 ml of tetrahydrofuran. The solution is mixed at room temperature with 1 ml (10 mmol) of n-butyllithium solution (10 M, n-hexane) under inert gas and while being stirred vigorously. The reaction solution is refluxed. After about 10 minutes of reaction time and cooling, the working-up is carried out by the addition in drops of 20 ml of saturated ammonium chloride solution and 30 ml of ethyl acetate. The organic phase is washed with water/common salt solution and dried on sodium sulfate. The crude product is purified by chromatography on silica gel (cyclohexane/ethyl acetate, 1:1). Yield 170 mg (60% of theory).

11β-Methoxy-3-triethylsilyloxy-estra-1,3,5(10),16-tetraene 284 mg (1 mmol) of 11β-methoxy-estra-1,3,5(10),16-tetraen-3-ol is reacted in 10 ml of tert-butylmethyl ether and 1 ml of pyridine with 0.6 ml of triethylbromosilane. After 1 hour, 30 ml of water is added to the reaction suspension. The organic phase is separated, washed, dried and concentrated by evaporation in a vacuum. The oily product that is thus obtained is used immediately in the next stage (hydroboration). Yield: 380 mg (95% of theory)

11β-Methoxy-estra-1,3,5(10)-triene-3,16α-diol (27)

380 mg (0.95 mmol) of 11-methoxy-3-triethylsilyloxy-estra-1,3,5(10),16-tetraene is dissolved in 20 ml of tetrahydrofuran under inert gas. After 464 mg (3.8 mmol) of 9-borabicyclo[3.3.1]nonane is added, the reaction solution is stirred at room temperature until the reaction is completed. Then, 5 ml of water is added in drops, and after gas generation is completed, 2 ml of 5N sodium hydroxide solution and 2 ml of 30% hydrogen peroxide solution are added in drops. It is stirred for 1 hour at room temperature, and the product that is produced is extracted with ethyl acetate. The crude product that is obtained is purified by chromatography on silica gel (n-hexane/chloroform/methanol 45/45/10) and crystallized from ethyl acetate/n-hexane. Colorless crystals are obtained: 230 mg (80% of theory).

Melting point 212–222° C.; $[\alpha]^{20}_D=+101°$ (dioxane, c=0.53)

EXAMPLE 28

11β-Methoxy-estra-1,3,5(10)-triene-3,16β-diol (28)

229 mg (0.76 mmol) of 11β-methoxy-estra-1,3,5(10)-triene-3,16α-diol is dissolved in 30 ml of toluene together with 1.8 g (6.8 mmol) of triphenylphosphine and 1.14 g (6.8 mmol) of 4-nitrobenzoic acid. 2.7 ml (6.8 mmol) of azodicarboxylic acid diethyl ester (40% in toluene) is added drop by drop to this solution. After a 24-hour reaction at room temperature, the reaction solution was mixed with ethyl acetate. The organic phase that is thus obtained is extracted with sodium bicarbonate solution, water and sodium chloride solution. The organic phase is concentrated by evaporation, and then the product is taken up in methanol. After 2.5 g of potassium carbonate is added, the suspension is refluxed until saponification is completed. For working-up, the methanol is distilled off, and the crude product is taken up in ethyl acetate, washed with water and sodium chloride solution, and the solution is concentrated by evaporation. After recrystallization from chloroform/cyclohexane, almost colorless crystals are obtained:

195 mg (85% of theory); melting point 195–200° C.; $[\alpha]^{20}_D=+86°$ (dioxane, c=1.18)

EXAMPLE 29

11β-Phenyl-estra-1,3,5(10)-triene-3,16α-diol

11β-Phenyl-17-tosylhydrazono-estra-1,3,5(10)-trien-3-ol 590 mg (1.71 mmol) is reacted with toluene-4-sulfonic acid hydrazide as described in Example 28. By cooling the reaction solution, in this case a proportion of the product precipitates. The solid product is suctioned off, washed with ethanol and dried. 450 mg of yellowish crystallizate (51% of theory) is obtained. The product that is still contained in the mother liquor can be isolated by extraction and corresponding chromatographic working-up (303 mg, 38% of theory).

11β-Phenyl-estra-1,3,5(10),16-tetraen-3-ol 515 mg (1 mmol) of 11-phenyl-17-tosylhydrazono-estra-1,3,5(10)-trien-3-ol is reacted with 1 ml (10 mmol) of n-butyllithium solution as in Example 28. 450 mg of crude product is obtained, which is reacted to triethylsilylether in the next stage.

11β-Phenyl-3-triethylsilyl-estra-1,3,5(10),16-tetraene

Corresponding to Example 28, 450 mg of 11β-phenyl-estra-1,3,5(10),16-tetraen-3-ol (crude product) is reacted to triethylsilylether. The product that is obtained is purified by chromatography on silica gel (cyclohexane/ethyl acetate, 6/1), and the solution is concentrated by evaporation in a vacuum. An oily substance is obtained. Yield 320 mg (72% of theory relative to 515 mg of 11β-phenyl-17-tosylhydrazono-estra-1,3,5(10)-trien-3-ol).

11β-Phenyl-estra-1,3,5(10)-triene-3,16α-diol (29)

The hydroboration is carried out according to Example 27. 320 mg (0.72 mmol) of 11β-phenyl-3-triethylsilyl-estra-1,3,5(10),16-tetraene yielded 183 mg (73% of theory) after working-up and purification by chromatography on silica gel (toluene/ethyl acetate, 70/30) and crystallization from methanol.

Melting point 254–261 $[\alpha]^{20}_D=-103°$ (dioxane, c=0.09)

EXAMPLE 30

11β-Phenyl-estra-1,3,5(O)-triene-3,16β-diol (30)

The inversion of the 16-hydroxy group was performed according to Example 28. 36 mg (0.1 mmol) of 11β-phenyl-estra-1,3,5(10)-triene-3,16α-diol yielded 25 mg (69% of theory) of colorless crystals after chromatography on silica gel (toluene/ethyl acetate, 70/30) and crystallization from toluene.

Melting point 241–247° $[\alpha]^{20}_D=-93°$ (dioxane, c=0.31)

EXAMPLE 31

16α-Ethinyl-18α-homo-estra-1,3,5(10)-triene-3,16β-diol (31)

At a temperature of about 0° C., 30 ml of tetrahydrofuran is saturated with ethine. Then, 3.4 ml (8.4 mmol) of n-butyllithium solution (2.5 M, toluene) is added to the solution while being cooled and stirred. The temperature should be about 0° C. A solution of 141 mg (0.5 mmol) of 3-hydroxy-18α-homo-estra-1,3,5(10)-trien-16-one in 10 ml of tetrahydrofuran is added to the suspension of lithium acetylide that is thus obtained. After 30 minutes of reaction time at about 0° C., the reaction solution is mixed with dilute hydrochloric acid. After the tetrahydrofuran is distilled off, the organic residue is taken up in toluene, the phases are separated, the organic phase is washed with water, and the crude product is isolated by concentration by evaporation of the solution under vacuum. A purification of the product is achieved by chromatography on silica gel (toluene/acetone, 7/1) and crystallization from toluene. 131 mg (85% of theory) of crystalline substance is obtained.

Melting point 197–202° C. $[\alpha]^{20}_D=+100°$ (dioxane, c=1.06)

EXAMPLE 32

16β-Ethinyl-18α-homo-estra-1,3,5(10)-triene-3,16α-diol (32)

The production of 16β-ethinyl-18α-homo-estra-1,3,5(10)-triene-3,16α-diol is performed analogously to Example 31. The increase of the reaction temperature to room temperature produced a larger proportion of 16β-ethinyl product. By chromatography on silica gel (cyclohexane/ethyl acetate, 3/1), it was possible to isolate the product.

Yield: 20% of theory, 213–219° C., $[\alpha]^{20}_D=+48°$ (dioxane, c=1.04)

EXAMPLE 33

11β-Fluoro-7α-methylestra-1,3,5(10)-triene-3,16β-diol

11β-Fluoro-7α-methylestra-1,3,5(10)-triene-3,16α-diol

11β-Fluoro-7α-methylestr-4-ene-3,17-dione

A suspension of 15.2 g (79.8 mmol) of copper iodide in 70 ml of dry tetrahydrofuran is cooled to 0° C., mixed with 28.7 g (330 mmol) of lithium bromide and 27.8 ml of DMPU, stirred first for 30 minutes at this temperature and then cooled to −30° C. While being stirred, 52 ml of methylmagnesium bromide in diethyl ether (3 molar solution) is then added in drops, stirred for another 30 minutes, and the gray-colored suspension is mixed with a solution that consists of 10.0 g (34.7 mmol) of 11β-fluoroestra-4,6-diene-3,17-dione, 24.3 ml of DMPU and 23 ml of trimethylsilyl chloride in 60 ml of dichloromethane. After the addition is completed, it is allowed to stir for another 1.5 hours between −30→−10° C., the cold bath is removed, and 35 ml of ethyl acetate is carefully added at room temperature while being stirred vigorously. For working-up, the reaction solution is diluted with ethyl acetate, washed with saturated aqueous ammonium chloride solution that is free of copper, and the organic phase is dried on sodium sulfate. The crude product is chromatographed on silica gel (hexane-ethyl acetate, gradient of up to 1:1), yield 3.1 g (30%).

11β-Fluoro-3-hydroxy-7α-methylestra-1,3,5(10)-trien-17-one 8.3 g (27.2 mmol) of 11β-fluoro-7α-methylestr-4-ene-3,17-dione in 260 ml of acetonitrile is mixed with 7.0 g (31.3 mmol) of copper(II) bromide, and the reaction mixture is stirred for 7 hours at room temperature. For working-up, the reaction solution is diluted with ethyl acetate, the organic phase is washed with aqueous ammonium chloride solution, sodium bicarbonate solution, and finally with water and dried on sodium sulfate. The crude product is chromatographed on silica gel (toluene-ethyl acetate, gradient of up to 7:3), yield 3.3 g (40%), [α]D+166.80 (c 0.5 methanol).

3-Ac tyloxy-11β-fluoro-7α-methylestra-1,3,5(10)-trien-17-one 3.0 g (9.9 mmol) of 11β-fluoro-3-hydroxy-7α-methylestra-1,3,5(10)-trien-17-one in 12 ml of pyridine and 6 ml of acetic acid anhydride are dissolved and allowed to react overnight at room temperature. For working-up, the reaction mixture is stirred into ice water, the precipitate is suctioned off, which then is taken up in ethyl acetate. The organic phase is first washed with dilute hydrochloric acid, then with water and dried on sodium sulfate. 3.4 g of product is obtained, which is sufficiently pure for further processing.

3-Acetyloxy-11β-fluoro-7α-methylestra-1,3,5(10),16-tetraene 3.8 g (18.4 mmol) of 2,6-di-tert-butyl-4-methylpyridine is added to a solution of 2.7 g (7.9 mmol) of 3-acetyloxy-11β-fluoro-7α-methyletra-1,3,5(10)-trien-17-one in 40 ml of dry dichloromethane, cooled under a cover gas atmosphere (argon) to 0° C., and 2.64 ml (16 mmol) of trifluoromethanesulfonic acid anhydride is added in drops while being stirred. The cold bath is removed, and stirred for 1.5 more hours at room temperature. For working-up, it is diluted with ethyl acetate, the organic phase is washed with water and dried on sodium sulfate. The crude product (6.0 g) is then taken up in 15 ml of dimethylformamide, mixed at room temperature with 5.72 ml of tributylamine, 0.11 g (0.15 mmol) of bis(acetato)-bis(triphenylphosphine) palladium, 0.61 ml (16 mmol) of formic acid and stirred for 30 minutes at a bath temperature of 60° C. (argon atmosphere). For working-up, it is poured into ice water, extracted with ethyl acetate, the organic phase is washed first with dilute hydrochloric acid, then with water and dried on sodium sulfate. The crude product is chromatographed on silica gel (heptane-acetone, gradient of up to 9:1), yield 1.71 g (66%).

11β-Fluoro-7α-methylestra-1,3,5(10)-triene-3,16β-diol

A solution of 1.67 g (5.22 mmol) of 3-acetyloxy-11βfluoro-7α-methylestra-1,3,5(10),16-tetraene in 30 ml of DMSO and 2.4 ml of water is replaced in portions with 1.36 g of N-bromosuccinimide while being stirred at 0° C., the cold bath is removed after the addition of NBS is completed, and it is stirred for 45 more minutes at room temperature. For working-up, the reaction mixture is poured into ice water, extracted with ethyl acetate, the organic phase is washed with water and dried on sodium sulfate. The crude bromohydrin (2.3 g) is then taken up in 25 ml of dry tetrahydrofuran, mixed with 5 ml (18.6 mmol) of tributyl tin hydride, a first spatula tip full of AIBN (a total of 200 mg dispersed over the reaction time), and stirred for 10 hours at a bath temperature of 80° C. under an argon atmosphere. For working-up, it is diluted with ethyl acetate, the organic phase is washed with dilute hydrochloric acid and water and dried on sodium sulfate. For saponification, the crude product is dissolved in 50 ml of methanol and 5 ml of dichloromethane, and it is mixed with 2.0 g of potassium carbonate. The reaction mixture is stirred for 1.5 hours under argon and poured into ice water for working-up. It is made hydrochloric with dilute acid, and it is extracted with ethyl acetate. The organic phase is washed with water and dried on sodium sulfate. The crude product is chromatographed on silica gel (chloroform-tert-butylmethylether, gradient of up to 95:5), yield 1.16 g (75%), melting point 239–240° C. while decomposing, $[\alpha]_D$+96.8° (c 0.51 methanol).

11β-Fluoro-7α-methylestra-1,3,5(10)-triene-3,16α-diol

A solution of 0.60 g (2.0 mmol) of 11-fluoro-7α-methylestra-1,3,5(10)-triene-3,16β-diol in 20 ml of dry tetrahydrofuran is mixed with 1.82 g (6.9 mmol) of triphenylphosphine and 0.26 ml of formic acid. Under an argon atmosphere, 1.10 ml of DEAD is then added in drops to this solution while being stirred at room temperature. After a reaction time of 30 minutes, it is mixed with water, extracted with ethyl acetate, the organic phase is washed with water and dried on sodium sulfate. The crude product is chromatographically purified on silica gel (dichloromethane-ethyl acetate, gradient of up to 95:5). The formates that are thus obtained are dissolved in 15 ml of dichloromethane, mixed with 7.5 ml of 3% methanolic potassium hydroxide solution, and left for 2 hours at room temperature under argon. For working-up, it is mixed with aqueous acetic acid, extracted with ethyl acetate, the organic phase is washed with water and dried on sodium sulfate. The crude product is purified by crystallization from acetone/hexane. Yield: 0.45 g (75%), melting point 221–222° C. while decomposing, $[\alpha]_D$+104.2° (c 0.52 methanol).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

TABLE 1

| Estrogen | Structure | hERα RBA* | hERβ RBA* | ERβ/ ERα | Rat uterus ER (RBA) | Rat prost. ER (RBA) | prost. ER/uterus ER |
|---|---|---|---|---|---|---|---|
| Estradiol | | 100 | 100 | 1 | 100 | 100 | 1 |
| Estrone | | 60 | 37 | 0.6 | 3 | 2 | 0.8 |
| 17α-Estradiol | | 58 | 11 | 0.2 | 2.4 | 1.3 | 0.5 |
| Estriol | | 14 | 21 | 1.5 | 4 | 20 | 5 |
| 5-Androstenediol | | 6 | 17 | 3 | 0.1 | 5 | 50 |
| Genisteine | | 5 | 36 | 7 | 0.1 | 10 | 100 |
| Coumestrol | | 94 | 185 | 2 | 1.3 | 24 | 18 |

*Cited from: Kuiper et al. (1996), Endocrinology 138: 863–870

TABLE 2

| Estrogen | Structure | hERα RBA* | hERβ RBA* | ERβ/ ERα | Rat uterus ER (RBA) | Rat prost. ER (RBA) | prost. ER/uterus ER |
|---|---|---|---|---|---|---|---|
| Estradiol | | 100 | 100 | 1 | 100 | 100 | 1 |
| Ethinylestradiol | | 111 | 46 | 0.4 | 345 | 35 | 0.1 |
| Cyclotriol | | 36 | 10 | 0.3 | 50 | 17 | 0.3 |
| Estrone | | 7 | 5 | 0.7 | 3 | 2 | 0.8 |
| Estriol | | 7 | 14 | 2 | 4 | 20 | 5 |
| 5-Androstenediol | | 1.7 | 10 | 6 | 0.1 | 5 | 50 |
| Genisteine | | 0.4 | 23 | 57 | 0.1 | 10 | 100 |
| Coumestrol | | 23 | 100 | 4.5 | 1.3 | 24 | 18 |
| Raloxifene | | 63 | 9 | 0.14 | 91 | 1.5 | 0.02 |
| Anordiol | | 15 | 0.2 | 0.01 | 6.6 | <0.01 | <0.01 |

TABLE 3

| Compound | Structure | In vitro Receptor binding ERβ (RBA)/ ERα (RBA) | Rat prost. ER (RBA) | Rat uterus ER (RBA) | In vitro 50% bone protection [µg/animal] | 50% uterus stimulation [µg/animal] |
|---|---|---|---|---|---|---|
| 16α-Estradiol | | 6 | 50 | 9 | 3 | 30 |

The invention claimed is:

1. A 3,16-Dihydroxyestra-1,3,5(10)-triene compound of formula I:

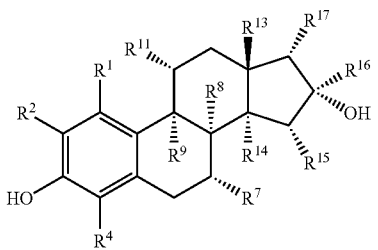

I in which radicals $R^1$ to $R^{17}$, independently of one another, have the following meanings:

$R^1$ is a halogen atom, a hydroxyl group, a methyl group, a trifluoromethyl group, a methoxy group, an ethoxy group or a hydrogen atom;

$R^2$ is a halogen atom, a hydroxyl group, a straight-chain or branched-chain, saturated or unsaturated alkoxy group with 1 to 6 carbon atoms or a hydrogen atom;

$R^4$ is a halogen atom, a straight-chain or branched-chain, saturated or unsaturated alkyl group with 1 to 10 carbon atoms, a trifluoromethyl or pentafluoroethyl group, a straight-chain or branched-chain, saturated or unsaturated alkoxy group with 1 to 6 carbon atoms or a hydrogen atom;

$R^7$ is a halogen atom in α- or β-position, a straight-chain or branched-chain, saturated or unsaturated, optionally partially or completely fluorinated alkyl group with 1 to 10 carbon atoms in α- or β-position, a straight-chain or branched-chain, saturated or unsaturated alkoxy group with 1 to 6 carbon atoms, an optionally substituted aryl or heteroaryl radical or a hydrogen atom;

$R^8$ is a hydrogen atom in α- or β-position, a straight-chain or branched-chain, saturated or unsaturated, optionally partially or completely fluorinated alkyl group with 1 to 10 carbon atoms in α- or β-position or a cyano group in α- or β-position;

$R^9$ is a hydrogen atom in α- or β-position, a methyl, ethyl, trifluoromethyl or pentafluoroethyl group in α- or β-position;

$R^{11}$ is a nitrooxy group in α- or β-position, a hydroxyl or mercapto group in α- or β-position, a halogen atom in α- or β-position, a chloromethyl group in α- or β-position, a straight-chain or branched-chain, saturated or unsaturated, optionally partially or completely fluorinated alkyl group with 1 to 10 carbon atoms in α- or β-position, a straight-chain or branched-chain, saturated or unsaturated alkoxy or alkylthio group with 1 to 6 carbon atoms, an optionally substituted aryl or heteroaryl radical or a hydrogen atom;

$R^{13}$ is a methyl, ethyl, trifluoromethyl or pentafluoroethyl group in β-position; and either $R^{14}$ is a straight-chain or branched-chain, saturated or unsaturated, optionally partially or completely fluorinated alkyl group with 1 to 10 carbon atoms in α- or β-position or a hydrogen atom in α- or β-position and $R^{15}$ is a halogen atom in α- or β-position, a straight-chain or branched-chain, saturated or unsaturated, optionally partially or completely fluorinated alkyl group with 1 to 10 carbon atoms in α- or β-position that can be interrupted by one or more oxygen atoms, sulfur atoms, sulfoxide or sulfone groups or imino groups =$NR^{15'}$ wherein $R^{15'}$=hydrogen atom, methyl, ethyl, propyl, i-propyl; or a hydrogen atom or $R^{14}$ and $R^{15}$ together is a 14α,15α-methylene or 14β,15β-methylene group that are optionally substituted with one or two halogen atoms;

$R^{16}$ is a straight-chain or branched-chain, saturated, optionally partially or completely fluorinated, alkyl group with 1 to 10 carbon atoms in α- or β-position, a trifluoromethyl or pentafluoroethyl group, a cyanomethyl group or a hydrogen atom in α- or β-position;

$R^{17}$ is a fluoro atom in α- or β-position, a straight-chain or branched-chain, saturated, optionally partially or completely fluorinated alkyl group with 1 to 10 carbon atoms in α- or β-position or a hydrogen atom, and the wavy lines mean the arrangement of the respective substituent in α- or β-position, excluding the compounds estra-1,3,5(10)-triene-3,16α-diol, and estra-1,3,5(10)-triene-3,16β-diol.

2. A compound according to claim 1, in which radicals $R^1$ to $R^{17}$, independently of one another, have the following meanings $R^1$ is a fluorine atom, a hydroxyl group, a methyl group, a trifluoromethyl group, a methoxy group, an ethoxy group or a hydrogen atom;

$R^2$ is a fluorine atom, a hydroxyl group, a methoxy or ethoxy group or a hydrogen atom;

$R^4$ is a fluorine atom, a methyl, ethyl, trifluoromethyl, methoxy or ethoxy group or a hydrogen atom;

$R^7$ is a fluorine atom in α- or β-position, a methyl, ethyl, propyl or i-propyl group in α- or β-position, an optionally substituted aryl radical, a trifluoromethyl group in α- or β-position or a hydrogen atom;

$R^8$ is a hydrogen atom in α- or β-position, a methyl or ethyl group in α- or β-position;

$R^9$ is a hydrogen atom in α- or β-position, a methyl, ethyl, trifluoromethyl or pentafluoroethyl group in α- or β-position;

$R^{11}$ is a nitrooxy group in α- or β-position, a hydroxyl group in α- or β-position, a fluorine atom in α- or β-position, a choromethyl group in α- or β-position, a methyl group in α- or β-position, a methoxy group in α- or α-position, a phenyl- or 3-methylthien-2-yl radical in α- or β-position or a hydrogen atom;

$R^{13}$ is a methyl or ethyl group in β-position; and either $R^{14}$ is a hydrogen atom in α- or β-position or a methyl group in α- or β-position and $R^{15}$ is a fluorine atom in α- or β-position, a methyl group in α- or β-position, or a hydrogen atom, or $R^{14}$ and $R^{15}$ together mean a 14α,15α-methylene group or a 14β,15β-methylene group, $R^{16}$ means a methyl, ethyl, or trifluoromethyl group;

$R^{17}$ means a fluorine atom in α- or β-position, a methyl group, or a hydrogen atom.

3. A compound of formula I according to claim 1, in which $R^7$ means a halogen atom in α- or β-position, a straight-chain or branched-chain, saturated or unsaturated, optionally partially or completely fluorinated alkyl group with 1 to 10 carbon atoms in α- or β-position, a straight-chain or branched-chain, saturated or unsaturated alkoxy group with 1 to 6 carbon atoms, or an optionally substituted aryl or heteroaryl radical and $R^1, R^2, R^4, R^8, R^9, R^{11}, R^{14}, R^{15}, R^{16}$ and $R^{17}$ in each case are a hydrogen atom.

4. A compound of formula I according to claim 1, in which $R^{11}$ is a nitrooxy group in α- or β-position, a hydroxyl or mercapto group in α- or β-position, a halogen atom in α- or β-position, a chloromethyl group in α- or β-position, a straight-chain or branched-chain, saturated or unsaturated, optionally partially or completely fluorinated alkyl group with 1 to 10 carbon atoms in α- or β-position, a straight-chain or branched-chain, saturated or unsaturated alkoxy or alkylthio group with 1 to 6 carbon atoms, or an optionally substituted aryl or heteroaryl radical, and $R^1, R^2, R^4, R^7, R^8, R^9, R^{14}, R^{15}, R^{16}$ and $R^{17}$ in each case are a hydrogen atom.

5. A compound of formula I according to claim 1, in which $R^{15}$ is a halogen atom in α- or β-position, a straight-chain or branched-chain, saturated or unsaturated, optionally partially or completely fluorinated alkyl group with 1 to 10 carbon atoms in α- or β-position that can be interrupted by one or more oxygen atoms, sulfur atoms, sulfoxide or sulfone groups or imino groups $=NR^{15'}$ ($R^{15'}$=hydrogen atom, methyl, ethyl, propyl, i-propyl), and $R^1, R^2, R^4, R^7, R^8, R^9, R^{11}, R^{14}, R^{16}$ and $R^{17}$ in each case are a hydrogen atom.

6. A compound of formula I according to claim 1, in which $R^7$ is a halogen atom in α- or β-position, a straight-chain or branched-chain, saturated or unsaturated, optionally partially or completely fluorinated alkyl group with 1 to 10 carbon atoms in α- or β-position, a straight-chain or branched-chain, saturated or unsaturated alkoxy group with 1 to 6 carbon atoms or an optionally substituted aryl or heteroaryl radical, $R^{11}$ is a nitrooxy group in α- or β-position, a hydroxyl or mercapto group in α- or β-position, a halogen atom in α- or β-position, a chloromethyl group in α- or β-position, a straight-chain or branched-chain, saturated or unsaturated, optionally partially or completely fluorinated alkyl group with 1 to 10 carbon atoms in α- or β-position, a straight-chain or branched-chain, saturated or unsaturated alkoxy or alkylthio group with 1 to 6 carbon atoms or an optionally substituted aryl or heteroaryl radical, and $R^1, R^2, R^4, R^8, R^9, R^{11}, R^{14}, R^{16}$ and $R^{17}$ in each case are a hydrogen atom.

7. Compounds of general formula I according to claim 1, in which $R^7$ is a halogen atom in α- or β-position, a straight-chain or branched-chain, saturated or unsaturated, optionally partially or completely fluorinated alkyl group with 1 to 10 carbon atoms in α- or β-position, a straight-chain or branched-chain, saturated or unsaturated alkoxy group with 1 to 6 carbon atoms or an optionally substituted aryl or heteroaryl radical, $R^{15}$ is a halogen atom in α- or β-position or a straight-chain or branched-chain, saturated or unsaturated, optionally partially or completely fluorinated alkyl group with 1 to 10 carbon atoms in α- or β-position that can be interrupted by one or more oxygen atoms, sulfur atoms, sulfoxide or sulfone groups or imino groups $=NR^{15'}$ ($R^{15'}$=hydrogen atom, methyl, ethyl, propyl, i-propyl), and $R^1, R^2, R^4, R^8, R^9, R^{11}, R^{14}, R^{16}$ and $R^{17}$ in each case are a hydrogen atom.

8. A compound of formula I according to claim 1, in which $R^{11}$ is a nitrooxy group in α- or β-position, a hydroxy or mercapto group in α- or β-position, a halogen atom in α- or β-position, a chloromethyl group in α- or β-position, a straight-chain or branched-chain, saturated or unsaturated, optionally partially or completely fluorinated alkyl group with 1 to 10 carbon atoms in α- or β-position, a straight-chain or branched-chain, saturated or unsaturated alkoxy or alkylthio group with 1 to 6 carbon atoms or an optionally substituted aryl or heteroaryl radical, $R^{15}$ is a halogen atom in α- or β-position or a straight-chain or branched-chain, saturated or unsaturated, optionally partially or completely fluorinated alkyl group with 1 to 10 carbon atoms in α- or β-position that can be interrupted by one or more oxygen atoms, sulfur atoms, sulfoxide or sulfone groups or imino groups $=NR^{15'}$ ($R^{15'}$=hydrogen atom, methyl, ethyl, propyl, i-propyl), and $R^1, R^2, R^4, R^7, R^8, R^9, R^{14}, R^{16}$, and $R^{17}$ in each case are a hydrogen atom.

9. A compound of formula I according to claim 1, in which $R^7$ is a halogen atom in α- or β-position, a straight-chain or branched-chain, saturated or unsaturated, optionally partially or completely fluorinated alkyl group with 1 to 10 carbon atoms in α- or β-position, a straight-chain or branched-chain, saturated or unsaturated alkoxy group with 1 to 6 carbon atoms or an optionally substituted aryl or heteroaryl radical, $R^{11}$ is a nitrooxy group in α- or β-position, a hydroxyl or mercapto group in α- or β-position, a halogen atom in α- or β-position, a chloromethyl group in α- or β-position, a straight-chain or branched-chain, saturated or unsaturated, optionally partially or completely fluorinated alkyl group with 1 to 10 carbon atoms in α- or β-position, a straight-chain or branched-chain, saturated or unsaturated alkoxy or alkylthio group with 1 to 6 carbon atoms or an optionally substituted aryl or heteroaryl radical, $R^{15}$ is a halogen atom in α- or β-position, or a straight-chain or branched-chain, saturated or unsaturated, optionally partially or completely fluorinated alkyl group with 1 to 10 carbon atoms in α- or β-position that can be interrupted by one or more oxygen atoms, sulfur atoms, sulfoxide or sulfone groups or imino groups =$NR^{15'}$ ($R^{15'}$=hydrogen atom, methyl, ethyl, propyl, i-propyl), and $R^1$, $R^2$, $R^4$, $R^8$, $R^9$, $R^{14}$, $R^{16}$ and $R^{17}$ in each case are a hydrogen atom.

10. A compound according to claims 1, wherein one or both hydroxyl groups is (are) esterified at C atoms 3 and 16 with an aliphatic or aromatic carboxylic acid or with an α- or β-amino acid.

11. A compound according to claim 1, which compound is:

14α,15α-methylen-estra-1,3,5(10)-triene-3,16α-diol,
14β,15β-methylen-estra-1,3,5(10)-triene-3,16α-diol,
7α-fluoro-estra-1,3,5(10)-triene-3,16α-diol,
11β-methoxy-estra-1,3,5(10)-triene-3,16α-diol,
7α-methyl-estra-1,3,5(10)-triene-3,16α-diol,
11β-fluoro-estra-1,3,5(10)-triene-3,16α-diol,
8α-estra-1,3,5(10)-triene-3,16α-diol,
estra-1,3,5(10)-triene-2,3,16α-triol,
17β-fluoro-estra-1,3,5(10)-triene-3,16α-diol,
18α-homo-estra-1,3,5(10)-triene-3,16α-diol,
18α-homo-14α,15α-methylen-estra-1,3,5(10)-triene-3,16α-diol,
14α,15α-methylen-estra-1,3,5(10)-triene-3,16β-diol,
14β,15β-methylen-estra-1,3,5(10)-triene-3,16β-diol,
7α-fluoro-estra-1,3,5(10)-triene-3,16β-diol,
11β-methoxy-estra-1,3,5(10)-triene-3,16β-diol,
7α-methyl-estra-1,3,5(10)-triene-3,16β-diol,
11β-fluoro-estra-1,3,5(10)-triene-3,16β-diol,
8α-estra-1,3,5(10)-triene-3,16β-diol,
estra-1,3,5(10)-triene-2,3,16α-triol,
17β-fluoro-estra-1,3,5(10)-triene-3,16β-diol,
18α-homo-estra-1,3,5(10)-triene-3,16β-diol,
18α-homo-14,15-methylen-estra-1,3,5(10)-triene-3,16β-diol,
7α-ethyl-estra-1,3,5(10)-triene-3,16α-diol,
7α-propyl-estra-1,3,5(10)-triene-3,16α-diol,
7α-i-propyl-estra-1,3,5(10)-triene-3,16α-diol,
7α-i-propenyl-estra-1,3,5(10)-triene-3,16α-diol,
7α-phenyl-estra-1,3,5(10)-triene-3,16α-diol,
7α-methoxy-estra-1,3,5(10)-triene-3,16α-diol
7α-thiomethyl-estra-1,3,5(10)-triene-3,16α-diol,
7α-cyanomethyl-estra-1,3,5(10)-triene-3,16α-diol,
7β-ethyl-estra-1,3,5(10)-triene-3,16α-diol,
7β-propyl-estra-1,3,5(10)-triene-3,16α-diol,
7β-i-propyl-estra-1,3,5(10)-triene-3,16α-diol,
7β-i-propenyl-estra-1,3,5(10)-triene-3,16α-diol,
7β-phenyl-estra-1,3,5(10)-triene-3,16α-diol,
7β-methoxy-estra-1,3,5(10)-triene-3,16α-diol,
7β-thiomethyl-estra-1,3,5(10)-triene-3,16α-diol,
7β-cyanomethyl-estra-1,3,5(10)-triene-3,16α-diol,
7α-ethyl-estra-1,3,5(10)-triene-3,16β-diol,
7α-propyl-estra-1,3,5(10)-triene-3,16β-diol,
7α-i-propyl-estra-1,3,5(10)-triene-3,16β-diol,
7α-i-propenyl-estra-1,3,5(10)-triene-3,16β-diol,
7α-phenyl-estra-1,3,5(10)-triene-3,16β-diol,
7α-methoxy-estra-1,3,5(10)-triene-3,16β-diol,
7α-thiomethyl-estra-1,3,5(10)-triene-3,16β-diol,
7α-cyanomethyl-estra-1,3,5(10)-triene-3,16β-diol,
7β-ethyl-estra-1,3,5(10)-triene-3,16β-diol,
7β-propyl-estra-1,3,5(10)-triene-3,16β-diol,
7β-i-propyl-estra-1,3,5(10)-triene-3,16β-diol,
7β-i-propenyl-estra-1,3,5(10)-triene-3,16β-diol,
7β-phenyl-estra-1,3,5(10)-triene-3,16β-diol,
7β-methoxy-estra-1,3,5(10)-triene-3,16β-diol,
7β-thiomethyl-estra-1,3,5(10)-triene-3,16β-diol,
7β-cyanomethyl-estra-1,3,5(10)-triene-3,16β-diol,
15α-methyl-estra-1,3,5(10)-triene-3,16α-diol,
15α-ethyl-estra-1,3,5(10)-triene-3,16α-diol,
15α-propyl-estra-1,3,5 (10)-triene-3,16α-diol,
15α-allyl-estra-1,3,5(10)-triene-3,16α-diol,
15α-i-propyl-estra-1,3,5(10)-triene-3,16α-diol,
15α-i-propenyl-estra-1,3,5(10)-triene-3,16α-diol,
15α-methoxy-estra-1,3,5(10)-triene-3,16α-diol,
15α-thiomethyl-estra-1,3,5(10)-triene-3,16α-diol,
15α-methyl-estra-1,3,5(10)-triene-3,16β-diol,
15α-ethyl-estra-1,3,5(10)-triene-3,16β-diol,
15α-propyl-estra-1,3,5(10)-triene-3,16β-diol,
15α-allyl-estra-1,3,5(10)-triene-3,16β-diol,
15α-i-propyl-estra-1,3,5(10)-triene-3,16β-diol,
15α-i-propenyl-estra-1,3,5(10)-triene-3,16β-diol,
15α-methoxy-estra-1,3,5(10)-triene-3,16β-diol,
15α-thiomethyl-estra-1,3,5(10)-triene-3,16β-diol,
15β-methyl-estra-1,3,5(10)-triene-3,16α-diol,
15β-ethyl-estra-1,3,5(10)-triene-3,16α-diol,
15β-propyl-estra-1,3,5(10)-triene-3,16α-diol,
15β-allyl-estra-1,3,5(10)-triene-3,16α-diol,
15β-i-propyl-estra-1,3,5(10)-triene-3,16α-diol,
15β-i-propenyl-estra-1,3,5(10)-triene-3,16α-diol,
15β-methoxy-estra-1,3,5(10)-triene-3,16α-diol,
15β-thiomethyl-estra-1,3,5(10)-triene-3,16α-diol,
15β-methyl-estra-1,3,5(10)-triene-3,16β-diol,
15β-ethyl-estra-1,3,5(10)-triene-3,16β-diol,
15β-propyl-estra-1,3,5(10)-triene-3,16β-diol,
15β-allyl-estra-1,3,5(10)-triene-3,16β-diol,
15β-i-propyl-estra-1,3,5(10)-triene-3,16β-diol,
15β-i-propenyl-estra-1,3,5(10)-triene-3,16β-diol,
15β-methoxy-estra-1,3,5(10)-triene-3,16β-diol,
15β-thiomethyl-estra-1,3,5(10)-triene-3,16β-diol,
7α-trifluoromethyl-11β-fluoro-estra-1,3,5(10)-triene-3,16α-diol,
7α-pentafluoroethyl-11β-fluoro-estra-1,3,5(10)-triene-3,16α-diol,
7α-ethyl-11β-fluoro-estra-1,3,5(10)-triene-3,16α-diol,
7α-propyl-11β-fluoro-estra-1,3,5(10)-triene-3,16α-diol,
7α-i-propyl-11β-fluoro-estra-1,3,5(10)-triene-3,16α-diol,
7α-i-propenyl-11β-fluoro-estra-1,3,5(10)-triene-3,16α-diol,
7α-phenyl-11β-Fluoro-estra-1,3,5(10)-triene-3,16α-diol,
7α-methoxy-11β-fluoro-estra-1,3,5(10)-triene-3,16α-diol,
7α-thiomethyl-11β-fluoro-estra-1,3,5(10)-triene-3,16α-diol,
7α-cyanomethyl-11β-fluoro-estra-1,3,5(10)-triene-3,16α-diol,
7β-ethyl-11β-fluoro-estra-1,3,5(10)-triene-3,16α-diol,
7β-propyl-11β-fluoro-estra-1,3,5(10)-triene-3,16α-diol,
7β-i-propyl-11β-fluoro-estra-1,3,5(10)-triene-3,16α-diol,
7β-i-propenyl-11β-fluoro-estra-1,3,5(10)-triene-3,16α-diol,
7β-phenyl-11β-fluoro-estra-1,3,5(10)-triene-3,16α-diol, 7β-methoxy-11β-fluoro-estra-1,3,5(10)-triene-3,16α-diol,
7β-thiomethyl-11β-fluoro-estra-1,3,5(10)-triene-3,16α-diol,
7β-cyanomethyl-11β-fluoro-estra-1,3,5(10)-triene-3,16α-diol,
7α-ethyl-11β-fluoro-estra-1,3,5(10)-triene-3,16β-diol,
7α-propyl-11β-fluoro-estra-1,3,5(10)-triene-3,16β-diol,
7α-i-propyl-11β-fluoro-estra-1,3,5(10)-triene-3,16β-diol,
7α-i-propenyl-11β-fluoro-estra-1,3,5(10)-triene-3,16β-diol,
7α-phenyl-11β-fluoro-estra-1,3,5(10)-triene-3,16β-diol,
7α-methoxy-11β-fluoro-estra-1,3,5(10)-triene-3,16β-diol,
7α-thiomethyl-11β-fluoro-estra-1,3,5(10)-triene-3,16β-diol,
7α-cyanomethyl-11β-fluoro-estra-1,3,5(10)-triene-3,16β-diol,
7β-ethyl-11β-fluoro-estra-1,3,5(10)-triene-3,16β-diol,
7β-propyl-11β-fluoro-estra-1,3,5(10)-triene-3,16β-diol,
7β-i-propyl-11β-fluoro-estra-1,3,5(10)-triene-3,16β-diol,
7β-i-propenyl-11β-fluoro-estra-1,3,5(10)-triene-3,16β-diol,
7β-phenyl-11β-fluoro-estra-1,3,5(10)-triene-3,16β-diol,
7β-methoxy-11β-fluoro-estra-1,3,5(10)-triene-3,16β-diol,
7β-thiomethyl-11β-fluoro-estra-1,3,5(10)-triene-3,16β-diol,
7β-cyanomethyl-11β-fluoro-estra-1,3,5(10)-triene-3,16β-diol,
15α-methyl-11β-fluoro-estra-1,3,5(10)-triene-3,16α-diol,
15α-ethyl-11β-fluoro-estra-1,3,5(10)-triene-3,16α-diol,
15α-propyl-11β-fluoro-estra-1,3,5(10)-triene-3,16α-diol,
15α-allyl-11β-fluoro-estra-1,3,5(10)-triene-3,16α-diol,
15α-i-propyl-11β-fluoro-estra-1,3,5(10)-triene-3,16α-diol,
15α-i-propenyl-11β-fluoro-estra-1,3,5(10)-triene-3,16α-diol,
15α-methoxy-11β-fluoro-estra-1,3,5(10)-triene-3,16α-diol,
15α-thiomethyl-11β-fluoro-estra-1,3,5(10)-triene-3,16α-diol,
15α-methyl-11β-fluoro-estra-1,3,5(10)-triene-3,16β-diol,
15α-ethyl-11β-fluoro-estra-1,3,5(10)-triene-3,16β-diol,
15α-propyl-11β-fluoro-estra-1,3,5(10)-triene-3,16β-diol,
15α-allyl-11β-fluoro-estra-1,3,5(10)-triene-3,16β-diol,
15α-i-propyl-11β-fluoro-estra-1,3,5(10)-triene-3,16β-diol,
15α-i-propenyl-11β-fluoro-estra-1,3,5(10)-triene-3,16β-diol,
15α-methoxy-11β-fluoro-estra-1,3,5(10)-triene-3,16β-diol,
15α-thiomethyl-11β-fluoro-estra-1,3,5(10)-triene-3,16β-diol,
15β-methyl-11β-fluoro-estra-1,3,5(10)-triene-3,16α-diol,
15β-ethyl-11β-fluoro-estra-1,3,5(10)-triene-3,16α-diol,
15β-propyl-11β-fluoro-estra-1,3,5(10)-triene-3,16α-diol,
15β-allyl-11β-fluoro-estra-1,3,5(10)-triene-3,16α-diol,
15β-i-propyl-11β-fluoro-estra-1,3,5(10)-triene-3,16α-diol,
15β-i-propenyl-11β-fluoro-estra-1,3,5(10)-triene-3,16α-diol,
15β-methoxy-11β-fluoro-estra-1,3,5(10)-triene-3,16α-diol,
15β-thiomethyl-11β-fluoro-estra-1,3,5(10)-triene-3,16α-diol,
15β-methyl-11β-fluoro-estra-1,3,5(10)-triene-3,16β-diol,
15β-ethyl-11β-fluoro-estra-1,3,5(10)-triene-3,16β-diol,
15β-propyl-11β-fluoro-estra-1,3,5(10)-triene-3,16β-diol,
15β-allyl-11β-fluoro-estra-1,3,5(10)-triene-3,16β-diol,
15β-i-propyl-11β-fluoro-estra-1,3,5(10)-triene-3,16β-diol,
15β-i-propenyl-11β-fluoro-estra-1,3,5(10)-triene-3,16β-diol,
15β-methoxy-11β-fluoro-estra-1,3,5(10)-triene-3,16β-diol,
15β-thiomethyl-11β-fluoro-estra-1,3,5(10)-triene-3,16β-diol,
14α,15α-methylene-7α-phenyl-estra-1,3,5(10)-triene-3,16α-diol,
14β,15β-methylene-7α-phenyl-estra-1,3,5(10)-triene-3,16α-diol,
11β-methoxy-7α-phenyl-estra-1,3,5(10)-triene-3,16α-diol,
11β-fluoro-7α-phenyl-estra-1,3,5(10)-triene-3,16α-diol,
7α-phenyl-8α-estra-1,3,5(10)-triene-3,16α-diol,
7α-phenyl-estra-1,3,5(10)-triene-2,3,16α-triol,
17β-fluoro-7α-phenyl-estra-1,3,5(10)-triene-3,16α-diol,
18α-homo-7α-phenyl-estra-1,3,5(10)-triene-3,16α-diol,
18α-homo-14α,15α-methylene-7α-phenyl-estra-1,3,5(10)-triene-3,16α-diol,
14α,15α-methylene-7α-phenyl-estra-1,3,5(10)-triene-3,16β-diol,
14β,15β-methylene-7α-phenyl-estra-1,3,5(10)-triene-3,16β-diol,
11β-methoxy-7α-phenyl-estra-1,3,5(10)-triene-3,16β-diol,
11β-fluoro-7α-phenyl-estra-1,3,5(10)-triene-3,16β-diol,
7α-phenyl-8α-estra-1,3,5(10)-triene-3,16β-diol,
7α-phenyl-estra-1,3,5(10)-triene-2,3,16α-triol,
17β-fluoro-7α-phenyl-estra-1,3,5(10)-triene-3,16β-diol,
18α-homo-7α-phenyl-estra-1,3,5(10)-triene-3,16β-diol,
18α-homo-14α,15α-methylene-7α-phenyl-estra-1,3,5(10)-triene-3,16β-diol,
15α-methyl-7α-phenyl-estra-1,3,5(10)-triene-3,16α-diol,
15α-ethyl-7α-phenyl-estra-1,3,5(10)-triene-3,16α-diol,
15α-propyl-7α-phenyl-estra-1,3,5(10)-triene-3,16α-diol,
15α-allyl-7α-phenyl-estra-1,3,5(10)-triene-3,16α-diol,
15α-i-propyl-7α-phenyl-estra-1,3,5(10)-triene-3,16α-diol,
15α-i-propenyl-7α-phenyl-estra-1,3,5(10)-triene-3,16α-diol,
15α-methoxy-7α-phenyl-estra-1,3,5(10)-triene-3,16α-diol,
15α-thiomethyl-7α-phenyl-estra-1,3,5(10)-triene-3,16α-diol,
15α-methyl-7α-phenyl-estra-1,3,5(10)-triene-3,16β-diol,
15α-ethyl-7α-phenyl-estra-1,3,5(10)-triene-3,16β-diol,
15α-propyl-7α-phenyl-estra-1,3,5(10)-triene-3,16β-diol,
15α-allyl-7α-phenyl-estra-1,3,5(10)-triene-3,16β-diol,
15α-i-propyl-7α-phenyl-estra-1,3,5(10)-triene-3,16β-diol,
15α-i-propenyl-7α-phenyl-estra-1,3,5(10)-triene-3,16β-diol,
15α-methoxy-7α-phenyl-estra-1,3,5(10)-triene-3,16β-diol,
15α-thiomethyl-7α-phenyl-estra-1,3,5(10)-triene-3,16β-diol,
15β-methyl-7α-phenyl-estra-1,3,5(10)-triene-3,16α-diol,
15β-ethyl-7α-phenyl-estra-1,3,5(10)-triene-3,16α-diol,
15β-propyl-7α-phenyl-estra-1,3,5(10)-triene-3,16α-diol,
15β-allyl-7α-phenyl-estra-1,3,5(10)-triene-3,16α-diol,
15β-i-propyl-7α-phenyl-estra-1,3,5(10)-triene-3,16α-diol, 15β-i-propenyl-7α-phenyl-estra-1,3,5(10)-triene-3,16α-diol,
15β-methoxy-7α-phenyl-estra-1,3,5(10)-triene-3,16α-diol,
15β-thiomethyl-7α-phenyl-estra-1,3,5(10)-triene-3,16α-diol,
15β-methyl-7α-phenyl-estra-1,3,5(10)-triene-3,16β-diol,
15β-ethyl-7α-phenyl-estra-1,3,5(10)-triene-3,16β-diol,
15β-propyl-7α-phenyl-estra-1,3,5(10)-triene-3,16β-diol,
15β-allyl-7α-phenyl-estra-1,3,5(10)-triene-3,16β-diol,
15β-i-propyl-7α-phenyl-estra-1,3,5(10)-triene-3,16β-diol,
15β-i-propenyl-7α-phenyl-estra-1,3,5(10)-triene-3,16β-diol,
15β-methoxy-7α-phenyl-estra-1,3,5(10)-triene-3,16β-diol,
15β-thiomethyl-7α-phenyl-estra-1,3,5(10)-triene-3,16β-diol,
15α-methyl-11β-fluoro-7α-phenyl-estra-1,3,5(10)-triene-3,16α-diol,
15α-ethyl-11β-fluoro-7α-phenyl-estra-1,3,5(10)-triene-3,16α-diol,
15α-propyl-11β-fluoro-7α-phenyl-estra-1,3,5(10)-triene-3,16α-diol,
15α-allyl-11β-fluoro-7α-phenyl-estra-1,3,5(10)-triene-3,16α-diol,
15α-i-propyl-11β-fluoro-7α-phenyl-estra-1,3,5(10)-triene-3,16α-diol,
15α-i-propenyl-11β-fluoro-7α-phenyl-estra-1,3,5(10)-triene-3,16α-diol,
15α-methoxy-11β-fluoro-7α-phenyl-estra-1,3,5(10)-triene-3,16α-diol,
15α-thiomethyl-11β-fluoro-7α-phenyl-estra-1,3,5(10)-triene-3,16α-diol,
15α-methyl-11β-fluoro-7α-phenyl-estra-1,3,5(10)-triene-3,16β-diol,
15α-ethyl-11β-fluoro-7α-phenyl-estra-1,3,5(10)-triene-3,16β-diol,
15α-propyl-11β-fluoro-7α-phenyl-estra-1,3,5(10)-triene-3,16β-diol,
15α-allyl-11β-fluoro-7α-phenyl-estra-1,3,5(10)-triene-3,16β-diol,
15α-i-propyl-11β-fluoro-7α-phenyl-estra-1,3,5(10)-triene-3,16β-diol,
15α-i-propenyl-11β-fluoro-7α-phenyl-estra-1,3,5(10)-triene-3,16β-diol,
15α-methoxy-11β-fluoro-7α-phenyl-estra-1,3,5(10)-triene-3,16β-diol,
15α-thiomethyl-11β-fluoro-7α-phenyl-estra-1,3,5(10)-triene-3,16β-diol,
15β-methyl-11β-fluoro-7α-phenyl-estra-1,3,5(10)-triene-3,16α-diol,
15β-ethyl-11β-fluoro-7α-phenyl-estra-1,3,5(10)-triene-3,16α-diol,
15β-propyl-11β-fluoro-7α-phenyl-estra-1,3,5(10)-triene-3,16α-diol,
15β-allyl-11β-fluoro-7α-phenyl-estra-1,3,5(10)-triene-3,16α-diol,
15β-i-propyl-11β-fluoro-7α-phenyl-estra-1,3,5(10)-triene-3,16α-diol,
15β-i-propenyl-11β-fluoro-7α-phenyl-estra-1,3,5(10)-triene-3,16α-diol,
15β-methoxy-11β-fluoro-7α-phenyl-estra-1,3,5(10)-triene-3,16α-diol,
15-thiomethyl-11β-fluoro-7α-phenyl-estra-1,3,5(10)-triene-3,16α-diol,
15β-methyl-11β-fluoro-7α-phenyl-estra-1,3,5(10)-triene-3,16β-diol,
15β-ethyl-11β-fluoro-7α-phenyl-estra-1,3,5(10)-triene-3,16β-diol,
15β-propyl-11β-fluoro-7α-phenyl-estra-1,3,5(10)-triene-3,16β-diol,
15β-allyl-11β-fluoro-7α-phenyl-estra-1,3,5(10)-triene-3,16β-diol,
15β-i-propyl-11β-fluoro-7α-phenyl-estra-1,3,5(10)-triene-3,16β-diol,
15β-i-propenyl-11β-fluoro-7α-phenyl-estra-1,3,5(10)-triene-3,16β-diol,
15β-methoxy-11β-fluoro-7α-phenyl-estra-1,3,5(10)-triene-3,16β-diol,
15β-thiomethyl-11β-fluoro-7α-phenyl-estra-1,3,5(10)-triene-3,16β-diol,
11β-[2-(3-methylthien)-yl)-estra-1,3,5(10)-triene-3,16α-diol,
11β-[2-(3-methylthien)-yl)-estra-1,3,5(10)-triene-3,16β-diol,
11β-methylestra-1,3,5(10)-triene-3,16α-diol,
11β-methylestra-1,3,5(10)-triene-3,16β-diol,
11β-methyl-18α-homoestra-1,3,5(10)-triene-3,16α-diol,
11β-methyl-18α-homoestra-1,3,5(10)-triene-3,16β-diol,
11β-ethylestra-1,3,5(10)-triene-3,16α-diol,
11β-ethylestra-1,3,5(10)-triene-3,16β-diol,
11β-ethyl-18α-homoestra-1,3,5(10)-triene-3,16α-diol,
11β-ethyl-18α-homoestra-1,3,5(10)-triene-3,16β-diol,
9α-methylestra-1,3,5(10)-triene-3,16α-diol, or
9α-methyl-18α-homoestra-1,3,5(10)-triene-3,16α-diol.

12. A compound according to claim 11, which compound is:
7α-fluoro-estra-1,3,5(10)-triene-3,16α-diol,
7α-methyl-estra-1,3,5(10)-triene-3,16α-diol,
7α-methyl-estra-1,3,5(10)-triene-3,16β-diol, or
18α-homo-estra-1,3,5(10)-triene-3,16α-diol.

13. A pharmaceutical composition containing at least one compound according to claim 1 and a pharmaceutically compatible vehicle.

* * * * *

UNITED STATES PATENT AND TRADEMARK OFFICE
CERTIFICATE OF CORRECTION

PATENT NO. : 7,109,360 B1 Page 1 of 1
APPLICATION NO. : 09/497891
DATED : September 19, 2006
INVENTOR(S) : Hermann Kuenzer et al.

It is certified that error appears in the above-identified patent and that said Letters Patent is hereby corrected as shown below:

Column 43, line 10, reads "a choromethyl group" should read -- a chloromethyl group --
Column 43, line 12, reads "α- or α-position," should read -- α- or β-position, --
Column 44, line 14, reads "$R^{14}$, $R^{16}$" should read -- $R^{14}$, $R^{15}$, $R^{16}$ --
Column 45, line 19, reads "claims 1," should read -- claim 1, --
Column 45, line 44, reads "2,3,16α-triol," should read -- 2,3,16β-triol, --
Column 50, line 11, reads "15-thiomethyl" should read -- 15β-thiomethyl --

Signed and Sealed this

Sixth Day of March, 2007

JON W. DUDAS
*Director of the United States Patent and Trademark Office*